United States Patent
Fukudo et al.

(10) Patent No.: US 11,215,607 B2
(45) Date of Patent: Jan. 4, 2022

(54) BIOMARKER FOR DIAGNOSIS OF IRRITABLE BOWEL SYNDROME

(71) Applicant: ONO PHARMACEUTICAL CO., LTD., Osaka (JP)

(72) Inventors: Shin Fukudo, Miyagi (JP); Seishi Katsumata, Osaka (JP); Hideaki Tada, Ibaraki (JP); Akio Hayashi, Ibaraki (JP); Chie Murata, Ibaraki (JP)

(73) Assignee: ONO PHARMACEUTICAL CO., LTD., Osaka (JP)

( * ) Notice: Subject to any disclaimer, the term of this patent is extended or adjusted under 35 U.S.C. 154(b) by 508 days.

(21) Appl. No.: 15/119,930

(22) PCT Filed: Feb. 18, 2015

(86) PCT No.: PCT/JP2015/054420
§ 371 (c)(1),
(2) Date: Aug. 18, 2016

(87) PCT Pub. No.: WO2015/125818
PCT Pub. Date: Aug. 27, 2015

(65) Prior Publication Data
US 2017/0059553 A1     Mar. 2, 2017

(30) Foreign Application Priority Data

Feb. 18, 2014 (JP) .............................. JP2014-028307
Oct. 30, 2014 (JP) .............................. JP2014-221829

(51) Int. Cl.
*G01N 33/493*      (2006.01)
*G01N 33/68*       (2006.01)

(52) U.S. Cl.
CPC ....... *G01N 33/493* (2013.01); *G01N 33/6848* (2013.01); *G01N 2800/065* (2013.01)

(58) Field of Classification Search
CPC ......... G01N 33/6848; G01N 2800/065; G01N 33/493
See application file for complete search history.

(56) References Cited

U.S. PATENT DOCUMENTS

2008/0226554 A1 *   9/2008   Colgan ............... C12Q 1/6886
                                                            424/9.1
2009/0180956 A1     7/2009   Ito et al.
(Continued)

FOREIGN PATENT DOCUMENTS

JP     2009-229456 A    10/2009
JP     4864083 B2        1/2012
(Continued)

OTHER PUBLICATIONS

Longstreth, et al.; "Functional Bowel Disorders", Gastroenterology, Apr. 2006, vol. 130, 1480-91, 12 pages total.
(Continued)

*Primary Examiner* — Rebecca M Fritchman
(74) *Attorney, Agent, or Firm* — Sughrue Mion, PLLC

(57) ABSTRACT

To provide a biomarker which is a metabolite included in a biological sample, and which can be collected in a noninvasive method and detected in a convenient analysis method, and which varies according to progression of pathological conditions of irritable bowel syndrome (IBS). Furthermore, such biomarkers are useful for determination of the presence or absence of morbidity of IBS, determination of severity of IBS, determination of types of IBS, determination of necessity of treatment of IBS, and confirmation of drug efficacy of an IBS therapeutic agent.

10 Claims, 1 Drawing Sheet

(56) References Cited

U.S. PATENT DOCUMENTS

2012/0315630 A1  12/2012  Gong et al.
2014/0141990 A1* 5/2014  Jones ................. G01N 33/6893
                                                            506/9

FOREIGN PATENT DOCUMENTS

| JP | 2012-047735 A | 3/2012 |
|---|---|---|
| JP | 2013-509593 A | 3/2013 |
| WO | 2009/098354 A1 | 8/2009 |
| WO | 2012/097207 A2 | 7/2012 |
| WO | 2012/127213 A1 | 9/2012 |

OTHER PUBLICATIONS

Fukudo, et al.; "Impact of Corticotropin-Releasing Hormone on Gastrointestinal Motility and Adrenocorticotropic Hormone in Normal Controls and Patients with Irritable Bowel Syndrome", Gut, 1998, vol. 42, 845-849, 5 pages total.
Posserud, et al.; "Altered Visceral Perceptual and Neuroendocrine Response in Patients with Irritable Bowel Syndrome During Mental Stress", Gut, 2004, vol. 53, 1102-08, 7 pages total.
Hamaguchi, et al.; "Changes in Salivary Physiological Stress Markers Induced by Muscle Stretching in Patients with Irritable Bowel Syndrome", BioPsychoSocial Medicine, Nov. 2008, vol. 2, No. 20, 8 pages total.
Clarke, et al.; "Tryptophan Degradation in Irritable Bowel Syndrome: Evidence of Indoleamine 2, 3-Dioxygenase Activation in a Male Cohort", BMC Gastroenterology, Jan. 2009, vol. 9, No. 6, 7 pages total.
Sugaya, et al.; "Adrenal Hormone Response and Psychophysiological Correlates Under Psychosocial Stress in Individuals with Irritable Bowel Syndrome", International Journal of Psychophysiology, Jan. 2012, vol. 84, 39-44, 6 pages total.
Heitkemper, et al.; "Increased Urine Catecholamines and Cortisol in Women with Irritable Bowel Syndrome", The American Journal of Gastroenterology, 1996, vol. 91, No. 5, 906-913, 8 pages total.
Wisniewska-Jarosinska, et al.; "Evaluation of Urinary 6-Hydroxymelatonin Sulphate Excretion in Women at Different Age with Irritable Bowel Syndrome", Journal of Physiology and Pharmacology, 2010, vol. 61, No. 3, 295-300, 6 pages total.
Radwan, et al.; "Is Melatonin Involved in the Irritable Bowel Syndrome?" Journal of Physiology and Pharmacology, 2009, vol. 60, Suppl. 3, 67-70, 4 pages total.
Stepien, et al.; "Melatonin Secretion and Metabolism in Patients with Irritable Bowel Syndrome", Polish Medical Journal, 2009, vol. 26, No. 155, 440-443, 4 pages total.
Moskwa, et al.; "Serum Serotonin Concentration and Urine 5-Hydroxyindole Acetic Acid Excretion in Patients with Irritable Bowel Syndrome", Polish Medical Journal, 2007, vol. 22, No. 131, 366-368, 3 pages total.
Yazar, et al.; "The Urinary 5-Hydroxyindole Acetic Acid and Plasma Nitric Oxide Levels in Irritable Bowel Syndrome: A Preliminary Study", Scottish Medical Journal, 2005, vol. 50, 27-29, 3 pages total.
Search Report dated May 19, 2015, issued by the International Searching Authority in counterpart International Application No. PCT/JP2015/054420 (PCT/ISA/210).
Written Opinion dated May 19, 2015, issued by the International Searching Authority in counterpart International Application No. PCT/JP2015/054420 (PCT/ISA/237).

* cited by examiner

-▲-: Healthy individual
-●-: IBS patient

-▲-: Healthy individual
-●-: IBS patient

BIOMARKER FOR DIAGNOSIS OF IRRITABLE BOWEL SYNDROME

TECHNICAL FIELD

The present invention relates to a biomarker (hereinafter, also referred to as a "biomarker of the present invention") capable of determining onset and aggravation of a symptom of irritable bowel syndrome in a human urine sample of a patient with irritable bowel syndrome.

BACKGROUND ART

Irritable bowel syndrome (hereinafter, also referred to as "IBS") is a stress-related digestive system disease caused by strong tension, anxiety, stress, and the like. This disease is one of the diseases receiving a lot of attention in today's society which is often likened to stress society. IBS is a disease whose main symptom is abnormality associated with gastrointestinal motor dysfunction symptoms mainly in large intestine, sometimes in small intestine, for example, defecation abnormality including chronic diarrhea symptom or constipation symptom accompanied with abdominal discomfort or stomachache, a symptom of gas accumulation accompanied with abdominal distension or a dull pain due to excessive gas in the intestine, or repetitive symptoms thereof.

Recently, search of therapeutic agents for IBS has proceeded, and therapeutic agents having various pharmacological actions have been developed. For example, 5-HT3 (receptor) antagonist, 5-HT4 agonist, TSPO antagonist, opioid antagonist, and the like, have been reported. However, at present, any of such drugs have not still provided a sufficient effect.

On the other hand, in most of IBSs, although no organic lesions such as findings of intestinal malformation are found in radiographic diagnosis or endoscopic diagnosis, symptoms of abnormality associated with defecation continue for a long time. Therefore, since a reliable test method for IBS has not been established and IBS is a disease diagnosed only from symptoms based on Rome III diagnosis criteria (see Non-Patent Literature 1), a biomarker capable of discriminating the onset of IBS is demanded.

Many studies of biomarkers capable of discriminating IBS have been reported so far. For example, a plasma adrenocorticotropic hormone (ACTH) level being increased more in IBS patients than in healthy individuals, due to the load of corticotropin release hormone (CRH), so that the plasma ACTH can be a biomarker (see Non-Patent Literatures 2 and 3); chromogranin A (CgA), a protein that is secreted from the sympathetic neuron being secreted in saliva more in IBS patients than in healthy individuals (see Non-Patent Literature 4); plasma kynurenic acid in male IBS patients being lower than that of healthy individuals (see Non-Patent Literature 5); dehydroepiandrosterone sulfate (DHEA-S) in saliva being decreased more in IBS patients than in healthy individuals after Trier Social Stress Test (TSST) (see Non-Patent Literature 6) have been reported.

Furthermore, for example, catecholamine such as norepinephrine and epinephrine and cortisol being increased in urine of female IBS patients as compared with healthy individuals (see Non-Patent Literature 7), the content of 6-sulfatoxymelatonin in urine of IBS patients being different from that of healthy individuals (see Non-Patent Literatures 8 to 10), serotonin in blood being higher in IBS patients than in healthy individuals, urinary 5-HIAA (serotonin metabolite) being lower in IBS patients than in healthy individuals (see Non-Patent Literatures 11 and 12), and the like, have been reported.

Furthermore, Patent Literature 1 describes detection of a stress disease biomarker from urine from an animal model reflecting pathological condition of IBS. Patent Literature 2 mentions that propionic acid in feces of an IBS patient can be used as an IBS determination marker.

However, biomarkers described in the above-mentioned Non-Patent Literatures and Patent Literatures have problems in view of use for noninvasive, convenient, rapid, and accurate IBS diagnosis in human subjects. Therefore, development of an IBS biomarker enabling rapid and accurate detection by a noninvasive and convenient method in human IBS patients, and being capable of reflecting the onset or pathological conditions of IBS, has been demanded.

CITATION LIST

Patent Literature

Patent Literature 1: JP-A-2012-047735
Patent Literature 2: JP-A-2009-229456

Non-Patent Literature

[Non-patent literature 1: Gastroenterology, 2006, Vol. 130, p. 1480-1491
[Non-patent literature 2] Gut, 1998, Vol. 42, p. 845-849
[Non-patent literature 3] Gut, 2004, Vol.53, p. 1102-1108
[Non-patent literature 4] BioPsychoSocial Medicine, 2008, Vol. 2, No. 20
[Non-patent literature 5] BMC Gastroenterology, 2009, Vol. 9, No. 6
[Non-patent literature 6] International Journal of Psychophysiology, 2012, Vol. 84, p. 39-44
[Non-patent literature 7] The American Journal of Gastroenterology, 1996, Vol. 91, No. 5, p. 906-913
[Non-patent literature 8] Journal of Physiology And Pharmacology, 2010, Vol. 61, No. 3, p. 295-300
[Non-patent literature 9] Journal of Physiology And Pharmacology, 2009, Vol. 60, Extra number No. 3, p. 67-70
[Non-patent literature 10] Pol Merkur Lekarski, 2009 May; 26(155): 440-3.
[Non-patent literature 11] Pol Merkur Lekarski, 2007 May; 22(131): 366-8
[Non-patent literature 12] Scott Med J, 2005 Feb; 50(1): 27-9

SUMMARY OF THE INVENTION

Technical Problems

In the above-mentioned circumstances, the main object of the present invention is to provide a biomarker which can be collected in a noninvasive method from a patient who may have IBS and detected in a convenient analysis method, and further a biomarker varying according to the progress of pathological conditions of IBS.

Problems to be Solved by the Invention

In order to solve the above-mentioned problems, the present inventors have keenly studied. As a result, the inventors have unexpectedly achieved a new finding that urine of IBS patients includes metabolite that varies when a gastrointestinal symptom is aggravated. Then, the present inventors have further studied, and have completed the present invention.

That is to say, the present invention relates to the following.

(1) A biomarker for diagnosis of irritable bowel syndrome, wherein the biomarker is a compound whose m/z value obtained when human urine, diluted with 0.1% (w/w) formic acid aqueous solution to which 0.09% (w/w) sodium azide has been added, is measured by LC/MS is:
121.1, 130.0, 130.1, 133.1, 149.0, 152.0, 156.1, 159.2, 162.1, 166.0, 168.1, 169.3, 170.1, 175.1, 180.8, 181.0, 181.2, 182.1, 182.3, 189.2, 192.0, 196.2, 197.0, 198.1, 205.1, 205.2, 210.1, 212.1, 216.1, 217.1, 221.4, 226.1, 226.4, 244.4, 247.5, 248.1, 251.3, 259.2, 260.1, 260.2, 264.3, 267.3, 268.2, 271.2, 280.1, 283.0, 283.2, 284.2, 286.2, 291.2, 292.0, 292.5, 295.1, 296.2, 298.1, 299.0, 300.5, 301.6, 302.7, 306.0, 313.6, 320.1, 325.2, 325.6, 326.4, 327.2, 328.4, 340.1, 342.1, 344.2, 344.4, 345.3, 346.2, 350.4, 352.5, 356.5, 358.5, 361.2, 364.1, 366.5, 368.5, 370.5, 381.3, 388.2, 389.3, 392.1, 402.2, 406.1, 419.9, 420.1, 424.1, 430.1, 444.2, 446.1, 458.1, 462.1, 469.3, 474.2, 503.3, 504.2, 526.2, 537.2, 558.2, 562.2, 562.3, or 601.3 (wherein the m/z value contains an error range of ±0.1), and the content of the compound in human urine varies with morbidity of irritable bowel syndrome.

(2) The biomarker as defined in the above (1), wherein when 250 µL of supernatant of human urine, which has been centrifuged at 2500 rpm for 15 min at 4° C. by a centrifugal machine, is mixed with 750 µL of 0.1% (w/w) formic acid aqueous solution to which 0.09% (w/w) sodium azide has been added to obtain a mixed solution, and the mixed solution is measured under the conditions in which:

LC/MS (ACQUITY UPLC manufactured by Waters), equipped with ACQUITY UPLC BEH C18 (1.7 µm, 2.1 mm×150 mm; manufactured by Waters) as an LC column and equipped with 4000QTRAP (manufactured by AB SCIEX) as an MS machine, is used;

a column temperature is 40° C.;

an automatic sampler temperature is 4° C.;

an injection amount of measuring sample is 5 µL;

a flow rate is 0.30 mL/min;

analysis time is 21 min; and gradient conditions (A/B (v/v %)) of a mobile phase (A) 0.1% (w/w) formic acid aqueous solution and a mobile phase (B) acetonitrile are 0-7 min (100/0), 7-14 min (0/100), and 14-21 min (100/0), the m/z value and the retention time are: 350.4 and 4.4 min, 264.3 and 3.9 min, 251.3 and 1.6 min, 283.2 and 1.7 min, 267.3 and 1.7 min, 268.2 and 1.6 min, 205.2 and 2.6 min, 189.2 and 2.7 min, 356.5 and 4.4 min, 356.5 and 4.7 min, 358.5 and 5.2 min, 326.4 and 4.1 min, 352.5 and 5.1 min, 328.4 and 3.1 min, 366.5 and 4.4 min, 344.4 and 3.8 min, 370.5 and 5.0 min, 166.0 and 0.6 min, 149.0 and 0.7 min, 325.2 and 4.1 min, 152.0 and 1.6 min, 133.1 and 0.7 min, 217.1 and 1.0 min, 168.1 and 1.7 min, 181.1 and 1.0 min, or 197.0 and 1.7 min (wherein the m/z value contains an error range of ±0.1 and the retention time contains an error range of ±0.1 min).

(3) The biomarker as defined in the above (1), wherein when 250 µL of supernatant of human urine, which has been centrifuged at 2500 rpm for 15 min at 4° C. by a centrifugal machine, is mixed with 750 µL of 0.1% (w/w) formic acid aqueous solution to which 0.09% (w/w) sodium azide has been added to obtain a mixed solution, and the mixed solution is measured under the conditions in which:

LC/MS (ACQUITY UPLC manufactured by Waters), equipped with ACQUITY UPLC BEH C18 (1.7 µm, 2.1 mm×100 mm; manufactured by Waters) as an LC column and equipped with LCT Premier (manufactured by Waters) as an MS machine, is used;

a column temperature is 40° C.;

an automatic sampler temperature is 4° C.;

an injection amount of measuring sample is 5 µL;

a flow rate is 0.30 mL/min;

analysis time is 17 min; and gradient conditions (A/B (v/v %)) of a mobile phase (A) 0.1% (w/w) formic acid aqueous solution, and a mobile phase (B) 0.1% (w/w) formic acid methanol solution are 0-4 min (100/0), 4-4.5 min (30/70), 4.5-10 min (2/98), and 10-17 min (100/0), the m/z value and the retention time are: 419.9 and 0.6 min, 198.1 and 1.3 min, 121.1 and 1.5 min, 226.4 and 1.6 min, 221.4 and 1.7 min, 182.3 and 1.8 min, 299.0 and 1.8 min, 364.1 and 1.8 min, 430.1 and 1.8 min, 462.1 and 1.8 min, 216.1 and 1.9 min, 175.1 and 2.0 min, 169.3 and 2.1 min, 291.2 and 2.1 min, 212.1 and 2.2 min, 280.1 and 2.2 min, 283.0 and 2.2 min, 406.1 and 2.2 min, 156.1 and 2.3 min, 295.1 and 2.3 min, 180.8 and 2.4 min, 181.2 and 2.4 min, 260.1 and 2.4 min, 392.1 and 2.4 min, 458.1 and 2.4 min, 170.1 and 2.5 min, 286.2 and 2.5 min, 300.5 and 2.5 min, 601.3 and 2.5 min, 159.2 and 2.6 min, 226.1 and 2.6 min, 320.1 and 2.6 min, 406.1 and 2.7 min, 420.1 and 2.7 min, 558.2 and 2.8 min, 537.2 and 2.9 min, 280.1 and 3.1 min, 526.2 and 3.3 min, 244.4 and 3.5 min, 284.2 and 3.6 min, 298.1 and 3.8 min, 388.2 and 3.8 min, 474.2 and 3.8 min, 444.2 and 3.9 min, 259.2 and 4.0 min, 292.5 and 4.0 min, 562.3 and 4.0 min, 248.1 and 4.1 min, 504.2 and 4.1 min, 325.2 and 4.2 min, 325.6 and 4.2 min, 446.1 and 4.2 min, 424.1 and 4.3 min, 301.6 and 4.4 min, 302.7 and 4.4 min, 313.6 and 4.5 min, 562.2 and 4.5 min, 503.3 and 4.6 min, 247.5 and 4.7 min, 271.2 and 4.7 min, 345.3 and 4.7 min, 327.2 and 4.8 min, 381.3 and 4.8 min, or 469.3 and 5.1 min (wherein the m/z value contains an error range of ±0.1, and the retention time contains an error range of ±0.1 min).

(4) The biomarker as defined in the above (1), wherein when 250 µL of supernatant of human urine, which has been centrifuged at 2500 rpm for 15 min at 4° C. by a centrifugal machine, is mixed with 750 µL of 0.1% (w/w) formic acid aqueous solution to which 0.09% (w/w) sodium azide has been added to obtain a mixed solution, and the mixed solution is measured under the conditions in which:

LC/MS (ACQUITY UPLC manufactured by Waters), equipped with ACQUITY UPLC BEH C18 (1.7 µm, 2.1 mm×100 mm; manufactured by Waters) as an LC column and equipped with LCT Premier (manufactured by Waters) as an MS machine, is used;

a column temperature is 40° C.;

an automatic sampler temperature is 4° C.;

an injection amount of measuring sample is 5 µL;

a flow rate is 0.30 mL/min;

analysis time is 17 min; and gradient conditions (A/B (v/v %)) of a mobile phase (A) 6.5 mM aqueous solution of ammonium hydrogencarbonate and a mobile phase (B) 6.5 mM aqueous solution of ammonium hydrogencarbonate in 95% (w/v) methanol are 0-4 min (100/0), 4-4.5 min (30/70), 4.5-10 min (2/98), and 10-17 min (100/0), the m/z value and the retention time are: 192.0 and 0.6 min, 196.2 and 0.6 min, 182.1 and 0.7 min, 210.1 and 0.7 min, 292.0 and 0.7 min, 306.0 and 0.7 min, 130.0 and 0.8 min, 205.1 and 0.9 min, 342.1 and 1.2 min, 162.1 and 1.5 min, 260.2 and 1.8 min, 340.1 and 2.1 min, 130.1 and 2.2 min, 296.2 and 2.6 min, 346.2 and 3.8 min, 344.2 and 4.2 min, 402.2 and 4.3 min, 361.2 and 4.4 min, 368.5 and 4.8 min, or 389.3 and 5.0 min (wherein the m/z value contains an error range of ±0.1 and the retention time contains an error range of ±0.1 min).

(5) The biomarker as defined in any one of the above (1) to (4), which is selected from the group consisting of 2-methylbutyrylglycine, dehydroepiandrosterone sulfate, 11-dehydro-thromboxane B2, estrone sulfate, 2,7,8-trimethyl-2-(β-carboxyethyl)-6-hydroxychroman, 2'-deoxyadenosine, guanosine, 2'-deoxyguanosine, inosine, xanthurenic acid, kynurenic acid, 8-iso-prostaglandin F1α, prostaglandin F1α, 13,14-dihydro-prostaglandin F1α, 2,3-dinor-11β-prostaglandin F2α, 13,14-dihydro-15-keto-prostaglandin D2, tetranor-prostaglandin D metabolite, 11-dehydro-thromboxane B3, 2,3-dinor-thromboxane B1, thromboxane B2, quinolinic acid, xylose, 2,3-dinor-8-iso-prostaglandin F2α, gentisic acid, glycylglycine, N-acetylarginine, 3-methoxytyramine, homovanillic acid, and vanillylmandelic acid.

(6) The biomarker as defined in any one of the above (1) to (4), which is selected from the group consisting of 2-methylbutyrylglycine, 11-dehydro-thromboxane B2, estrone sulfate, 2'-deoxyadenosine, guanosine, 2'-deoxyguanosine, inosine, xanthurenic acid, 8-iso-prostaglandin F1α, prostaglandin F1α, 13,14-dihydro-prostaglandin F1α, 2,3-dinor-11β-prostaglandin F2α, 13,14-dihydro-15-keto-prostaglandin D2, tetranor-prostaglandin D metabolite, 11-dehydro-thromboxane B3, 2,3-dinor-thromboxane B1, thromboxane B2, quinolinic acid, xylose, 2,3-dinor-8-iso-prostaglandin F2α, gentisic acid, glycylglycine, N-acetylarginine, 3-methoxytyramine, homovanillic acid, and vanillylmandelic acid.

(7) A method for screening a therapeutic agent for irritable bowel syndrome, the method including a step of measuring a concentration of the biomarker as defined in any one of the above (1) to (6) in human urine.

(8) Use of the biomarker as defined in any one of the above (1) to (6) for manufacturing a diagnostic agent for irritable bowel syndrome.

(9) A diagnostic agent for irritable bowel syndrome, for quantifying the biomarker as defined in any one of the above (1) to (6) in urine.

(10) A method for screening and selecting a drug, the method including measuring the biomarker as defined in any one of the above (1) to (6) to determine a category and/or severity of irritable bowel syndrome, and screening and selecting a drug suitable for a patient.

(11) Use of the biomarker for measuring the biomarker as defined in any one of the above (1) to (6) to determine a category and/or severity of irritable bowel syndrome, and screening and selecting a drug suitable for a patient.

(12) A kit for diagnosis of irritable bowel syndrome, including a reagent for measuring a concentration of the biomarker as defined in any one of the above (1) to (6) in human urine.

(13) The kit for diagnosis as defined in the above (12), wherein a therapeutic agent for irritable bowel syndrome is screened and selected depending on a category and/or severity of irritable bowel syndrome.

(14) A method for diagnosing irritable bowel syndrome, the method including a step of measuring a concentration of the biomarker as defined in any one of the above (1) to (6) in human urine.

(15) A method for diagnosing irritable bowel syndrome, the method including measuring concentrations of the biomarkers as defined in any one of the above (1) to (6) in human urine, and calculating a ratio of the concentrations of any two or more types of biomarkers in human urine.

(16) A method for diagnosing irritable bowel syndrome, the method including measuring concentrations of quinolinic acid, xanthurenic acid, and kynurenic acid in human urine, and calculating a quinolinic acid/xanthurenic acid ratio or a quinolinic acid/kynurenic acid ratio.

Advantageous Effects of the Invention

A biomarker of the present invention enables diagnosis of IBS to be carried out in a noninvasive and convenient method rapidly and accurately. Furthermore, since the biomarker of the present invention can reflect the onset or pathological conditions of IBS exactly, the present invention can provide a biomarker useful for determination of the presence or absence of morbidity of IBS, determination of severity of IBS, determination of types of IBS, determination of necessity of treatment of IBS, and confirmation of drug efficacy of an IBS therapeutic agent.

DESCRIPTION OF EMBODIMENTS

Figure 1:
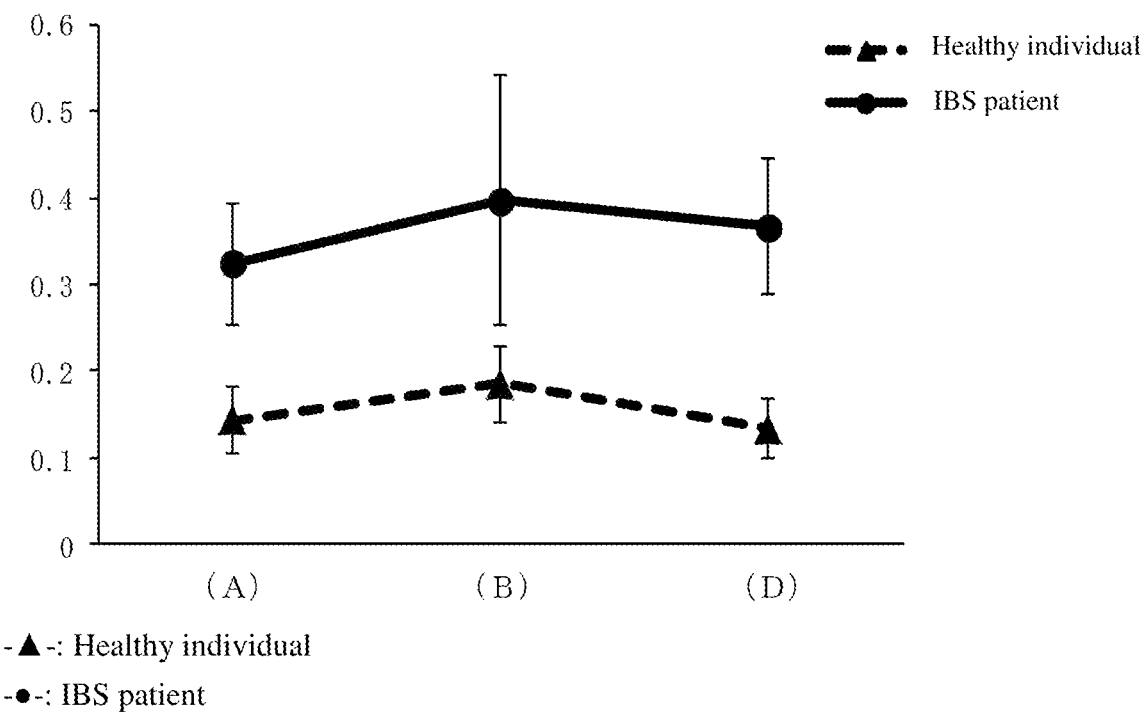
FIG. 1 shows results of comparison of a quinolinic acid/xanthurenic acid ratio between healthy individuals and IBS patients. The ordinate shows a quinolinic acid/xanthurenic acid ratio and the abscissa shows urine collection points shown in Example 1 (4).

Hereinafter, the present invention is described in detail.

A biomarker of the present invention includes a material whose content in a human biological sample varies depending on morbidity of IBS and the degree of pathological condition of IBS. Examples of the biological sample may include urine, blood, saliva, cerebral spinal fluid, and the like. In the present invention, as the biological sample, human urine is preferably used.

Herein, as mentioned above, some studies in which the content of certain materials in human urine are compared between IBS patients and healthy individuals, have been reported so far.

For example, it is reported that the concentrations of catecholamine (norepinephrine and epinephrine) and cortisol in urine of female IBS patient were higher as compared with those of healthy individuals in The American Journal of Gastroenterology, 1996, Vol. 91, No. 5, p. 906-913. However, it is known that the concentration of catecholamine in urine is also increased in pheochromocytoma, neuroblastoma, adrenal medullary hyperplasia, heart failure, myocardial infarct, Parkinson's disease, essential hypertension, hypothyroidism, schizophrenia, depression, diabetes, and the like (see, for example, IGAKU-SHOIN's MEDICAL DICTIONARY (2nd edition), p. 399); it is known that the concentration of cortisol that is a kind of ACTH in urine is also increased in Cushing's syndrome, stress, depression, neural anorexia, and the like. That is to say, catecholamine and cortisol in urine do not have specificity as a biomarker of IBS.

Furthermore, it has been reported that the concentration of 6-sulfatoxymelatonin in urine of female patients with IBS with constipation and IBS with diarrhea is higher than that of healthy female individuals in Journal of Physiology And Pharmacology, 2010, Vol. 61, No. 3, p. 295-300, as well as Pol Merkur Lekarski, 2009 May; 26(155): 440-3. However, on the other hand, it has been reported that the concentration of 6-sulfatoxymelatonin in urine of patients (male and female patients) with IBS with constipation and IBS with diarrhea is lower than that of healthy individuals in Journal of Physiology And Pharmacology, 2009, Vol. 60, Supplementary volume No. 3, p. 67-70. The results of the above-mentioned literatures have no consistency, showing that use of 6-sulfatoxymelatonin as a biomarker of IBS has a problem.

It has been reported that serotonin in blood of IBS patients is higher than that of healthy individuals; the concentration of 5-HIAA (serotonin metabolite) in urine is lower than that of healthy individuals; and there is a possibility that serotonin metabolizing ability is decreased in IBS patients in Pol Merkur Lekarski, 2007 May; 22(131): 366-8 an Scott Med J, 2005 February; 50(1): 27-9. However, in order to determine the metabolic rate of serotonin, it is necessary to compare the amount of the serotonin in blood and the amount of 5-HIAA in urine with each other. Therefore, use of them is insufficient for a noninvasive and convenient, and rapid and accurate diagnosis of IBS.

Thus, it has been reported that some materials show difference in the content in urine between IBS patients and healthy individuals, but a biomarker permitting a noninvasive, convenient, rapid, and accurate diagnosis of IBS has not been known.

On the other hand, in the present invention, examining of a biomarker of the present invention in human urine enables IBS to be diagnosed objectively. That is to say, according to the present invention, a noninvasive, convenient, rapid, and accurate diagnosis of IBS can be carried out without depending upon the skill of a person who carries out diagnosis.

It is generally known that there are 4 categories of IBS categorized as IBS with constipation, IBS with diarrhea, mixed IBS or unclassified IBS. The biomarker of the present invention can be applied to any of these IBSs. Furthermore, the biomarker of the present invention can be used suitably for diagnosis and the like of IBS regardless of sex (male or female) of patients and ages of patients.

In one preferable embodiment of the present invention, when diagnosis of IBS is carried out using the biomarker, two types or more of biomarkers, and more preferably three types or more of biomarkers are used. Diversified determination using a plurality of biomarkers preferably improves the accuracy of diagnosis.

Hereinafter, a biomarker of the present invention is described specifically.

The biomarker of the present invention is not particularly limited as long as the biomarker is contained in human urine and detected by LC/MS analysis in the below-mentioned conditions, and its content in human urine varies depending upon morbidity of IBS or the degree of pathological conditions of IBS.

The biomarker of the present invention includes (1) a material such as metabolite in a biological sample specified by the name of compound, and (2) a material such as metabolite in a biological test sample specified by the mass (m/z value) and the retention time measured in the LC/MS conditions described in the below-mentioned Examples.

In one preferable embodiment of the present invention, specific examples of the biomarker include 2-methylbutyrylglycine (CAS registry number: 52320-67-9), dehydroepiandrosterone sulfate (DHEA-S) (CAS registry number: 651-48-9), 11-dehydro-thromboxane B2 (CAS registry number: 67910-12-7), estron sulfate (CAS registry number: 481-97-0), 2,7,8-trimethyl-2-(β-carboxyethyl)-6-hydroxychroman (γ-CEHC) (CAS registry number: 178167-75-4), 2'-deoxyadenosine (CAS registry number: 958-09-8), guanosine (CAS registry number: 118-00-3), 2'-deoxyguanosine (CAS registry number: 961-07-9), inosine (CAS registry number: 58-63-9), xanthurenic acid (CAS registry number: 59-00-7), kynurenic acid (CAS registry number: 492-27-3), 8-iso-prostaglandin F1α (CAS registry number: 26771-96-0), prostaglandin F1α (CAS registry number: 745-62-0), 13,14-dihydro-prostaglandin F1α (CAS registry number: 20592-20-5), 2,3-dinor-11β-prostaglandin F2α (CAS registry number: 240405-20-3), 13,14-dihydro-15-keto-prostaglandin D2 (CAS registry number: 59894-07-4), tetranor-prostaglandin D metabolite (CAS registry number: 70803-91-7), 11-dehydro-thromboxane B3 (CAS registry number: 129228-55-3), 2,3-dinor-thromboxane B1 (CAS registry number: 63250-09-9), thromboxane B2 (CAS registry number: 54397-85-2), quinolinic acid (CAS registry number: 89-00-9), xylose (CAS registry number: 58-86-6), 2,3-dinor-8-iso-prostaglandin F2α (CAS registry number: 221664-05-7), gentisic acid (CAS registry number: 490-79-9), glycylglycine (CAS registry number: 556-50-3), N-acetylarginine (CAS registry number: 155-84-0), 3-methoxytyramine (CAS registry number: 554-52-9), homovanillic acid (CAS registry number: 306-08-1), and vanillylmandelic acid (CAS registry number: 55-10-7). Among them, 2-methylbutyrylglycine, 11-dehydro-thromboxane B2, estrone sulfate, 2'-deoxyadenosine, guanosine, 2'-deoxyguanosine, inosine, xanthurenic acid, 8-iso-prostaglandin F1α, prostaglandin F1α, 13,14-dihydro-prostaglandin F1α, 2,3-dinor-11β-prostaglandin F2α, 13,14-dihydro-15-keto-prostaglandin D2, tetranor-prostaglandin D metabolite, 11-dehydro-thromboxane B3, 2,3-dinor-thromboxane B1, thromboxane B2, quinolinic acid, xylose, 2,3-dinor-8-iso-prostaglandin F2α, gentisic acid, glycylglycine, N-acetylarginine, 3-methoxytyramine, homovanillic acid, and vanillylmandelic acid are preferably used from the viewpoint of accurate diagnosis of IBS.

In the present invention, the urinary concentration of each biomarker among the biomarkers is measured, and then the concentration ratio of any two or more biomarkers is calculated, thus enabling diagnosis of IBS to be carried out. For example, as shown in the below-mentioned Examples, the concentrations of quinolinic acid, xanthurenic acid and/or kynurenic acid in human urine are measured, and the quinolinic acid/xanthurenic acid ratio and/or quinolinic acid/kynurenic acid ratio are calculated. Thereby, the diagnosis of IBS can be carried out accurately.

In another preferable embodiment of the present invention, the biomarker includes compounds such as metabolite having unknown or known structures, which are specified by the mass (m/z value) and the retention time measured in the LC/MS conditions described in the below-mentioned Examples.

More specifically, the biomarker of the present invention includes a compound in which the m/z values obtained when human urine, diluted with 0.1% formic acid aqueous solution to which 0.09% sodium azide has been added, and measured by LC/MS is:

121.1, 130.0, 130.1, 133.1, 149.0, 152.0, 156.1, 159.2, 162.1, 166.0, 168.1, 169.3, 170.1, 175.1, 180.8, 181.0, 181.2, 182.1, 182.3, 189.2, 192.0, 196.2, 197.0, 198.1, 205.1, 205.2, 210.1, 212.1, 216.1, 217.1, 221.4, 226.1, 226.4, 244.4, 247.5, 248.1, 251.3, 259.2, 260.1, 260.2, 264.3, 267.3, 268.2, 271.2, 280.1, 283.0, 283.2, 284.2, 286.2, 291.2, 292.0, 292.5, 295.1, 296.2, 298.1, 299.0, 300.5, 301.6, 302.7, 306.0, 313.6, 320.1, 325.2, 325.6, 326.4, 327.2, 328.4, 340.1, 342.1, 344.2, 344.4, 345.3, 346.2, 350.4, 352.5, 356.5, 358.5, 361.2, 364.1, 366.5, 368.5, 370.5, 381.3, 388.2, 389.3, 392.1, 402.2, 406.1, 419.9, 420.1, 424.1, 430.1, 444.2, 446.1, 458.1, 462.1, 469.3, 474.2, 503.3, 504.2, 526.2, 537.2, 558.2, 562.2, 562.3, or 601.3 (wherein the m/z value contains an error range of ±0.1), and a content of the compound in urine varies with morbidity of IBS.

Specifically, the above-mentioned measurement conditions of LC/MS include the following measurement conditions 1 to 3.

<Measurement Conditions 1>
LC/MS (ACQUITY UPLC manufactured by Waters) equipped with
LC column: ACQUITY UPLC BEH C18 (1.7 μm, 2.1 mm×150 mm; manufactured by Waters) and
LC/MS machine: 4000QTRAP (manufactured by AB SCIEX),
Column temperature: 40° C.,
Automatic sampler temperature: 4° C.,
Injection amount of measuring sample: 5 μL,
Flow rate: 0.30 mL/min,
Analysis time: 21 min,
Mobile phase (A): 0.1% formic acid aqueous solution,
Mobile phase (B): acetonitrile,
Gradient conditions (A/B (v/v %)): 0-7 min (100/0)→7-14 min (0/100)→14-21 min (100/0),
Polarity: positive, negative,
Scan type: MRM,
Ionization method: ESI (electrospray ionization) method,
Source temperature: 400° C., In the above-mentioned gradient condition, for example, description "0-7 min (100/0)→7-14 min (0/100)→14-21 min (100/0)" represents that liquid is fed in the condition in which the mobile phase (A) is 100% (v/v) and the mobile phase (B) is 0% (v/v) for 7 min from the start of the analysis time (0 min); liquid is fed in the condition in which the mobile phase (A) is 0% (v/v) and the mobile phase (B) is 100% (v/v) from the time when 7 min have passed to the time when 14 min have passed after the start of analysis; and liquid is fed in the condition in which the mobile phase (A) is 100% (v/v) and the mobile phase (B) is 0% (v/v) from the time when 14 min have passed to the time when 21 min have passed after the start of analysis. The same is true to the following in this specification.

<Measurement Conditions 2>
LC/MS (ACQUITY UPLC manufactured by Waters) equipped with
LC column: ACQUITY UPLC BEH C18 (1.7 μm, 2.1 mm×100 mm; manufactured by Waters) and
LC/MS machine: LCT Premier (manufactured by Waters),
Column temperature: 40° C.,
Automatic sampler temperature: 4° C.,
Injection amount of measuring sample: 5 μl,
Flow rate: 0.30 ml/min,
Analysis time: 17 min,
Mobile phase (A): 0.1% formic acid aqueous solution,
Mobile phase (B): 0.1% formic acid methanol solution,
Gradient condition (A/B (v/v %)): 0-4 min (100/0)→4-4.5 min (30/70)→4.5-10 min (2/98)→10-17 min (100/0),
Polarity: Positive,
Analyzer: V mode,
Capillary: 2300 V,
Sample cone: 30 V,
Desolvation temperature: 350° C.,
Source temperature: 120° C.,
Cone gas flow rate: 50 L/h,
Desolvation gas flow rate: 800 L/h <Measurement Conditions 3>
LC/MS (ACQUITY UPLC manufactured by Waters) equipped with
LC column: ACQUITY UPLC BEH C18 (1.7 μm, 2.1 mm x100 mm; manufactured by Waters) and
LC/MS machine: LCT Premier (manufactured by Waters)
Column temperature: 40° C.,
Automatic sampler temperature: 4° C.,
Injection amount of measuring sample: 5 μl,
Flow rate: 0.30 ml/min,
Analysis time: 17 min,
Mobile phase (A): 6.5 mM aqueous solution of ammonium hydrogencarbonate
Mobile phase (B): 6.5 mM aqueous solution of ammonium hydrogencarbonate in 95% (w/v) methanol
Gradient condition (A/B (v/v %)): 0-4 min (100/0)→4-4.5 min (30/70)→4.5-10 min (2/98)→10-17 min (100/0),
Polarity: Negative,
Analyzer: V mode,
Capillary: 2200 V,
Sample cone: 70 V,
Desolvation temperature: 200° C.,
Source temperature: 100° C.,
Cone gas flow rate: 50 L/h,
Desolvation gas flow rate: 200 L/h Note here that in the present invention, the test sample to be used for the above-mentioned LC/MS analysis can be prepared by subjecting human urine placed in a 50 mL-sampling tube to centrifugation using a centrifugal separator at 4° C. and 2500 rpm for 15 min, and then mixing 250 μL of the supernatant of the urine with 750 μL of 0.1% (w/w) formic acid aqueous solution to which 0.09% (w/w) sodium azide has been added.

In one embodiment of the present invention, the biomarker may be a compound in which the m/z value and the retention time when the measuring test sample of human urine prepared by the above-mentioned method and measured under the measurement condition 1 is:
350.4 and 4.4 min, 264.3 and 3.9 min, 251.3 and 1.6 min, 283.2 and 1.7 min, 267.3 and 1.7 min, 268.2 and 1.6 min, 205.2 and 2.6 min, 189.2 and 2.7 min, 356.5 and 4.4 min, 356.5 and 4.7 min, 358.5 and 5.2 min, 326.4 and 4.1 min, 352.5 and 5.1 min, 328.4 and 3.1 min, 366.5 and 4.4 min, 344.4 and 3.8 min, 370.5 and 5.0 min, 166.0 and 0.6 min, 149.0 and 0.7 min, 325.2 and 4.1 min, 152.0 and 1.6 min, 133.1 and 0.7 min, 217.1 and 1.0 min, 168.1 and 1.7 min, 181.1 and 1.0 min, or 197.0 and 1.7 min (wherein the m/z value contains an error range of ±0.1 and the retention time contains an error range of ±0.1 min).

In another embodiment of the present invention, the biomarker may be a compound in which the m/z value and the retention time when a measuring test sample of human urine prepared by the above-mentioned method and measured under the measurement condition 2 is:
419.9 and 0.6 min, 198.1 and 1.3 min, 121.1 and 1.5 min, 226.4 and 1.6 min, 221.4 and 1.7 min, 182.3 and 1.8 min, 299.0 and 1.8 min, 364.1 and 1.8 min, 430.1 and 1.8 min, 462.1 and 1.8 min, 216.1 and 1.9 min, 175.1 and 2.0 min, 169.3 and 2.1 min, 291.2 and 2.1 min, 212.1 and 2.2 min, 280.1 and 2.2 min, 283.0 and 2.2 min, 406.1 and 2.2 min, 156.1 and 2.3 min, 295.1 and 2.3 min, 180.8 and 2.4 min, 181.2 and 2.4 min, 260.1 and 2.4 min, 392.1 and 2.4 min, 458.1 and 2.4 min, 170.1 and 2.5 min, 286.2 and 2.5 min, 300.5 and 2.5 min, 601.3 and 2.5 min, 159.2 and 2.6 min, 226.1 and 2.6 min, 320.1 and 2.6 min, 406.1 and 2.7 min, 420.1 and 2.7 min, 558.2 and 2.8 min, 537.2 and 2.9 min, 280.1 and 3.1 min, 526.2 and 3.3 min, 244.4 and 3.5 min, 284.2 and 3.6 min, 298.1 and 3.8 min, 388.2 and 3.8 min, 474.2 and 3.8 min, 444.2 and 3.9 min, 259.2 and 4.0 min, 292.5 and 4.0 min, 562.3 and 4.0 min, 248.1 and 4.1 min, 504.2 and 4.1 min, 325.2 and 4.2 min, 325.6 and 4.2 min, 446.1 and 4.2 min, 424.1 and 4.3 min, 301.6 and 4.4 min, 302.7 and 4.4 min, 313.6 and 4.5 min, 562.2 and 4.5 min, 503.3 and 4.6 min, 247.5 and 4.7 min, 271.2 and 4.7 min, 345.3 and 4.7 min, 327.2 and 4.8 min, 381.3 and 4.8 min, or 469.3 and 5.1 min (wherein the m/z value contains an error range of ±0.1, and the retention time contains an error range of ±0.1 min).

In still another embodiment of the present invention, the biomarker may be a compound in which the m/z value and the retention time when a measuring test sample of human urine prepared by the above-mentioned method and measured under the measurement condition 3 is:

192.0 and 0.6 min, 196.2 and 0.6 min, 182.1 and 0.7 min, 210.1 and 0.7 min, 292.0 and 0.7 min, 306.0 and 0.7 min, 130.0 and 0.8 min, 205.1 and 0.9 min, 342.1 and 1.2 min, 162.1 and 1.5 min, 260.2 and 1.8 min, 340.1 and 2.1 min, 130.1 and 2.2 min, 296.2 and 2.6 min, 346.2 and 3.8 min, 344.2 and 4.2 min, 402.2 and 4.3 min, 361.2 and 4.4 min, 368.5 and 4.8 min, or 389.3 and 5.0 min (wherein the m/z value contains an error range of ±0.1 and the retention time contains an error range of ±0.1 min).

In the present invention, timing of collecting the urine test sample to be used for the above-mentioned measurement is not particularly limited. When determination of the presence or absence of morbidity of IBS, determination of severity of IBS, determination of necessity of treatment of IBS, and the like, are carried out, it is preferable to collect a test sample when a subject him/herself feels that the gastrointestinal symptom is aggravated, from the viewpoint of reflecting the onset and pathological condition of IBS more clearly.

Since the biomarker of the present invention reflects the onset and pathological conditions of IBS, it can be used for determination of the presence or absence of morbidity of IBS, determination of severity of IBS, determination of necessity of treatment of IBS, or confirmation of the therapeutic effect of an IBS therapeutic agent, and the like.

In order to carry out determination of the presence or absence of morbidity of IBS, determination of severity of IBS, determination of types of IBS, determination of necessity of treatment of IBS, confirmation of a therapeutic effect of an IBS therapeutic agent, and the like, using the biomarker of the present invention, the biomarker of the present invention in the measuring test sample of human urine may be quantified or the concentration of the biomarker in urine may be measured.

Also, by comparing the measurement value of the biomarker with a reference value, the determination of the presence or absence of morbidity of IBS, the determination of severity of IBS, the determination of types of IBS, the determination of necessity of treatment of IBS, and the like, may be carried out. The "reference value" can use the measurement value of the biomarker of a healthy individual diagnosed to have no organic diseases and psychiatric disorder, and no gastrointestinal symptom by a physician based on Rome III Criteria.

Note here that a specific method of the quantification or measurement of the concentration in urine of the biomarker can include the method described in the below-mentioned Examples. Furthermore, as for the measurement value, techniques such as creatinine correction, which are usually used in this field, may be used. Since the creatinine correction is sufficiently established, the present invention may conform to the creatinine correction.

The present invention also includes a screening method in drug development of therapeutic agents for IBS. In one embodiment, the screening method of the present invention preferably includes a step of measuring the concentration of the biomarker in human urine, and a step of administering a candidate drug of the IBS therapeutic agent to a patient. In this embodiment, the measurement of the biomarker is preferably carried out before and after administration of the candidate drug. Measurement values of the biomarker are compared between before and after the administration of the candidate drug. And then, after administration of the drug, drugs that decrease the measurement value of the biomarker whose content in human urine is increased by morbidity of IBS and/or the drugs that increase the measurement value of the biomarker whose content is decreased by morbidity of IBS, are expected to be effective as the IBS therapeutic agent. As the biomarker whose content in human urine is increased or decreased by morbidity of IBS, Examples mentioned below can be referred.

Furthermore, the biomarker of the present invention can be used in selection of a therapeutic agent suitable for an individual patient. The therapeutic effect of a therapeutic agent may be different depending on types (categories) of IBS patients and/or the degree of the pathological conditions. One embodiment of the present invention also includes a method for confirming the therapeutic effect of therapeutic agent in individual patients by measuring the biomarker.

Furthermore, one embodiment of the present invention relates to a method for screening and selecting a drug by determining the category and/or severity of IBS by measuring the biomarker, and screening and selecting a drug suitable for a patient.

In addition, another embodiment of the present invention relates to use of the biomarker for screening and selecting a drug suitable for a patient by determining kinds and/or the severity of IBS by measuring the biomarker.

Examples of the IBS therapeutic agent whose therapeutic effect can be confirmed by the biomarker of the present invention include TSPO (Translocator protein 18 kDa) antagonist, benzodiazepine antianxiety drug, thienodiazepin antianxiety drug, non-benzodiazepine antianxiety drug, CRF antagonist, neurokinin-1 (NK1) antagonist, tricyclic antidepressant drug, tetracyclic antidepressant drug, monoamine oxidase (MAO) inhibitor, triazolopyridine antidepressant drug, serotonin and noradrenaline reuptake inhibitor (SNRI), selective serotonin reuptake inhibitor (SSRI), serotonin reuptake inhibitor, noradrenaline reuptake inhibitor, noradrenergic and specific serotonergic antidepressant drug (NaSSA), noradrenaline and dopamine disinhibition drug (NDDI), selective serotonin reuptake enhancer (SSRE), N-methyl-D-aspartate (NMDA) receptor inhibitor, glycine transporter inhibitor, dopamine precursor, dopamine receptor agonist, catechol-O-methyltransferase (COMT) inhibitor, choline esterase inhibitor, neurotensin antagonist, anticholinergic drug, serotonin-dopamine antagonist, central nervous system stimulator, antiepileptic drug, antivertigo medicine, digestive function modulator, histamine $H_2$ receptor antagonist, proton-pump inhibitor, muscarine receptor antagonist, defensive factor enhancer, prostaglandin derivatives, opioid μ receptor agonist and opioid δ receptor antagonist, opioid agonist, 5-$HT_4$ agonist, 5-$HT_3$ (receptor) antagonist, chloride channel activator, guanylate cyclase inhibitor, bulk laxatives, saline laxatives, stimulant laxatives, and affinity polyacrylic resin.

In the present invention, examples of the TSPO antagonist include ONO-2952.

In the present invention, examples of the benzodiazepine antianxiety drug include alprazolam, oxazepam, oxazolam, cloxazolam, clorazepate dipotassium, chlordiazepoxide, diazepam, tofisopam, triazolam, prazepam, fludiazepam, flutazolam, flutoprazepam, bromazepam, mexazolam, medazepam, ethyl loflazepate, and lorazepam.

In the present invention, examples of the thienodiazepin antianxiety drug include etizolam, and clotiazepam.

In the present invention, examples of the non-benzodiazepine antianxiety drug include tandospirone citrate, and hydroxyzine hydrochloride.

In the present invention, examples of the CRF antagonist include Pexacerfont, Verucerfont, Emicerfont, E-2508, and ONO-2333.

In the present invention, examples of the neurokinin-1 antagonist include aprepitant, and fosaprepitant meglumine.

In the present invention, examples of the tricyclic antidepressant drug include amitriptyline hydrochloride, imipramine hydrochloride, clomipramine hydrochloride, dosulepine hydrochloride, nortriptyline hydrochloride, lofepramine hydrochloride, trimipramine maleate, and amoxapine.

In the present invention, examples of the tetracyclic antidepressant drug include maprotiline hydrochloride, mianserin hydrochloride, and setiptiline maleate.

In the present invention, examples of the monoamine oxidase (MAO) inhibitor include safrazine hydrochloride.

In the present invention, examples of the triazolopyridine antidepressant drug include trazodone hydrochloride.

In the present invention, examples of the serotonin and noradrenaline reuptake inhibitor (SNRI) include milnacipran hydrochloride, duloxetine hydrochloride, and venlafaxine hydrochloride.

In the present invention, examples of the selective serotonin reuptake inhibitor (SSRI) include fluvoxamine maleate, paroxetine hydrochloride, fluoxetine hydrochroride, citalopram hydrochloride, and escitalopram oxalate.

In the present invention, examples of the serotonin reuptake inhibitor include trazodone hydrochloride.

In the present invention, examples of the noradrenaline reuptake inhibitor include atomoxetine.

In the present invention, examples of the noradrenergic and specific serotonergic antidepressant drug include mirtazapine.

In the present invention, examples of the noradrenaline and dopamine disinhibition drug include agomelatine.

In the present invention, examples of the selective serotonin reuptake enhancer include tianeptine.

In the present invention, examples of the N-methyl-D-aspartate receptor inhibitor include memantine.

In the present invention, examples of the glycine transporter inhibitor include bitopertin, and ORG25935.

In the present invention, examples of the dopamine precursor include levodopa.

In the present invention, examples of the dopamine receptor agonist include bromocriptine.

In the present invention, examples of the COMT inhibitor include entacapone and opicapone.

In the present invention, examples of the choline esterase inhibitor include donepezil and rivastigmine.

In the present invention, examples of the neurotensin antagonist include SR48692.

In the present invention, examples of the anticholinergic drug include trihexyphenidyl, biperiden, ipratropium bromide, and mepenzolate bromide.

In the present invention, examples of the serotonin and dopamine antagonist include risperidone, paliperidone, perospirone hydrochloride hydrate, quetiapine fumarate, and olanzapine.

In the present invention, examples of the antiepileptic drug include phenobarbital, phenytoin, carbamazepine, valproic acid, clonazepam, levetiracetam, topiramate, and lamotrigine.

In the present invention, examples of the antivertigo medicine include difenidol, and betahistine.

In the present invention, examples of the digestive function modulator include trimebutine maleate, and polycarbophil calcium.

In the present invention, examples of the histamine $H_2$ receptor antagonist include cimetidine, ranitidine, famotidine, nizatidine, and lafutidine.

In the present invention, examples of the proton-pump inhibitor include omeprazole, lansoprazole, and rabeprazole.

In the present invention, examples of the muscarine receptor antagonist include pirenzepine.

In the present invention, examples of the defensive factor enhancer include gefarnate, teprenone, sucralfate, aldioxa, cetraxate hydrochloride, and ornoprostil.

In the present invention, examples of the prostaglandin derivatives include ornoprostill and misoprostol.

In the present invention, examples of the opioid μ receptor agonist and opioid δ receptor antagonist include eluxadoline.

In the present invention, examples of the opioid agonist include asimadoline, and nalfurafine.

In the present invention, examples of the $5\text{-}HT_4$ agonist include tegaserod, cisapride, and mosapride citrate.

In the present invention, examples of the $5\text{-}HT_3$ antagonist include ramosetron, alosetron, and cilansetron.

In the present invention, examples of the chloride channel activator include lubiprostone.

In the present invention, examples of the guanylate cyclase agonist include linaclotide.

In the present invention, examples of the bulk laxatives include methylcellulose, carmellose, and lactulose.

In the present invention, examples of the saline laxatives include magnesium sulfate, and magnesium oxide.

In the present invention, examples of the stimulant laxatives include picosulfate, lactulose, castor oil, senna, and rhubarb.

In the present invention, examples of the affinity polyacrylic resin include polycarbophil calcium.

Furthermore, another embodiment of the present invention relates to use of the biomarker for manufacturing a diagnostic agent for IBS. It is preferable that the diagnostic agent quantifies the biomarker. More specifically, it is preferable that the diagnostic agent detects an error of the concentration of the biomarker in urine with respect to the reference value (higher or lower than the reference value). Furthermore, as the diagnostic agent of the present invention, for example, commercially available measurement kits shown in the following Table 1, which are presently used for the other applications, may be applied. That is to say, by using quantification kits shown in Table 1, quantification of the biomarker of the invention of the present application may be carried out.

TABLE 1

| Compound name | Quantification kit | Manufacture name |
|---|---|---|
| DHEAS | Dehydroepiandrosterone Sulphate (DHEA-S) ELISA | IBL-International |
| 11-dehydro TXB2 | 11-dehydro-TXB2 ELISA Kit | abcam |
| Estrone sulfate | Estrone Sulphate (E1S) ELISA Kit | antibodies-online |
| gamma-CEHC | gamma-CEHC EIA Kit (plasma and serum) | Cayman |
| Inosine | Inosine Quantification Assay Kit (Fluorometric) | abcam |
| Xanthurenic acid | ELISA Kit for Xanthurenic Acid (XA) | USCN |
| Kynurenic acid | ELISA Kit for Kynurenic Acid (KYNA) | USCN |
| 8-Iso prostaglandin F1α | 516351 8-isoprostane EIA Kit | Cayman |
| Thromboxane B2 | Thromboxane B2 Express EIA Kit | Cayman |

Furthermore, the present invention includes a kit for diagnosis of IBS including a reagent for measuring the concentration of the biomarker in human urine. In one preferable embodiment of the present invention, it is preferable that the kit for diagnosis of IBS includes application of screening and selecting a therapeutic agent for IBS depending on the category and/or severity of IBS of a patient.

Furthermore, the present invention includes a method for diagnosing irritable bowel syndrome. The method includes a step of measuring the concentration of the biomarker in human urine. A method for measuring the concentration of the biomarker in human urine may be the same as the above.

EXAMPLES

The following Experimental Examples and Examples further illustrate the present invention, but the present invention is not limited to these Examples, and many modifications can be made thereto by a person having ordinary skill in the art without departing from the scope of the technical idea of the present invention.

Example 1

<Comparison Study Between IBS Patients and Healthy Individuals>

(1) Subjects: Subjects included 25 IBS patients (15 male patients and 10 female patients) and 25 healthy individuals (15 male subjects and 10 female subjects). The ages of male healthy individuals ranged from 18 to 55; the ages of male IBS patients ranged from 17 to 54; the ages of female healthy individuals ranged from 18 to 48; and the ages of female IBS patients range from 17 to 48. This study was performed with the approval from the Ethics Committee of Tohoku University Graduate School of Medicine. All the subjects provided written informed consent.

(2) Criteria of patients: IBS patients were classified by a physician based on Rome III Criteria. On the other hand, healthy individuals were classified as individuals who were diagnosed by a physician to have neither organic diseases nor psychiatric disorders, and no gastrointestinal symptoms.

(3) Method for collecting and handling urine: Urine samples were collected as spot urine into a urine collection cup from each subject for every urine collection point mentioned below and collected into a special-purposed urine collection test sample tube (about 10 mL/time), and cryopreserved until preparation.

(4) Urine collection point: In both IBS patients and healthy individuals, on urine collection days mentioned below, urine from the time after breakfast to the time before lunch, was arbitrarily collected.

(A) The day of consent to participation to study.

(B) The day when a subject self-evaluated that gastrointestinal symptom got aggravated during the period from (A) to (D).

(C) The day when the subjects self-evaluated that gastrointestinal symptom became worse than (B) during the period from (A) to (D).

(D) The day of medical examination one month after from the day of consent of (A).

(5) Preparation of human test sample: Cryopreserved human test sample was thawed in a refrigerator at 4° C., transferred to 50 mL-sampling tube (manufactured by Becton, Dickinson and Company, Japan), stirred, and centrifuged at 2500 rpm for 15 min at 4° C. by a cooled centrifuge. The supernatant in the amount of 250 μL was taken in a sampling tube (manufactured by BIO-BIK), 750 μL of human test sample diluted solution (0.1% formic acid aqueous solution to which 0.09% sodium azide has been added) was added thereto, and the mixture was stirred to obtain a solution as a LC/MS measurement test sample.

(6) Measurement condition of LC/MS

[LC Measurement Conditions 1]

Machine to be used: ACQUITY UPLC (manufactured by Waters)

Column: ACQUITY UPLC BEH C18 (1.7 μm, 2.1 mm×150 mm) (manufactured by Waters)

Column temperature: 40° C.

Automatic sampler temperature: 4° C.

Mobile phase (A): 0.1% formic acid aqueous solution (B): acetonitrile

Injection amount of measuring sample: 5 μL

Gradient conditions of mobile phase A/B

TABLE 2

| Time (min) | 0 | 7 | 14 | 14.1 | 21 |
|---|---|---|---|---|---|
| A (%) | 100 | 0 | 0 | 100 | 100 |
| B (%) | 0 | 100 | 100 | 0 | 0 |

In Table, % denotes vol. %

Flow rate: 0.30 ml/min

Analysis time: 21 min

MS machine: 4000QTRAP (manufactured by AB SCIEX)

Polarity: positive, negative

[LC Measurement Condition 2]

Machine to be used: ACQUITY UPLC (manufactured by Waters)

Column: ACQUITY UPLC BEH C18 (1.7 μm, 2.1 mm×100 mm) (manufactured by Waters)

Column temperature: 40° C.

Automatic sampler temperature: 4° C.

Mobile phase (A): 0.1% formic acid aqueous solution
 (B): 0.1% formic acid methanol solution
Injection amount of measuring sample: 5 μL
Gradient conditions of mobile phase A/B

TABLE 3

| | Time (min) | | | | |
|---|---|---|---|---|---|
| | 0 | 4 | 4.5 | 10 | 10.1 | 17 |
| A (%) | 100 | 30 | 2 | 2 | 100 | 100 |
| B (%) | 0 | 70 | 98 | 98 | 0 | 0 |

In Table, % denotes vol. %.
 Flow rate: 0.35 ml/min
 Analysis time: 17 min
 MS machine: 4000QTRAP, LCT Premier (manufactured by Waters)
 Polarity: positive
[LC Measurement Condition 3]
 Machine to be used: ACQUITY UPLC (manufactured by Waters)
 Column: ACQUITY UPLC BEH C18 (1.7 μm, 2.1 mm×100 mm) (manufactured by Waters)
 Column temperature: 40° C.
 Automatic sampler temperature: 4° C.
 Mobile phase (A): 6.5 mM aqueous solution of ammonium hydrogencarbonate
  (B): 6.5 mM aqueous solution of ammonium hydrogencarbonate in 95% methanol
 Injection amount of measuring sample: 5 μL
 Gradient conditions of mobile phase A/B

TABLE 4

| | Time (min) | | | | |
|---|---|---|---|---|---|
| | 0 | 4 | 4.5 | 10 | 10.1 | 17 |
| A (%) | 100 | 30 | 2 | 2 | 100 | 100 |
| B (%) | 0 | 70 | 98 | 98 | 0 | 0 |

In Table, % denotes vol. %.
 Flow rate: 0.35 ml/min
 Analysis time: 17 min
 MS machine: 4000QTRAP, LCT Premier
 Polarity: negative
[MS Measurement Conditions 1]
 MS machine: 4000QTRAP
 Polarity: positive, negative
 Scan type: MRM
 Ionization method: ESI (electrospray ionization) method
 Source temperature: 400° C.
[MS Measurement Conditions 2]
 MS machine: LCT Premier
 Polarity: positive
 Analyzer: V mode
 Capillary: 2300 V
 Sample cone: 30 V
 Desolvation temperature: 350° C.
 Source temperature: 120° C.
 Cone gas flow rate: 50 L/h
 Desolvation gas flow rate: 800 L/h
[MS Measurement Condition 3]
 MS machine: LCT Premier
 Polarity: negative
 Analyzer: V mode
 Capillary: 2200 V
 Sample cone: 70 V,
 Desolvation temperature: 200° C.
 Source temperature: 100° C.
 Cone gas flow rate: 50 L/h,
 Desolvation gas flow rate: 200 L/h
(7) Evaluation of gastrointestinal symptom and stress and the like in IBS patients and healthy individuals Firstly, the severity of the IBS symptom was measured based on IBS Severity Index (see IBS-SI: Aliment Pharmacol Ther 1997; 11: pp. 395-402), property of IBS symptom was measured based on Self-reported IBS Questionnaire (see SIBSQ: Journal of Clinical Gastroenterology, 2008, Vo.42, No. 9, pp. 1010-6), general gastrointestinal symptom was measured based on Gastrointestinal Symptoms Rating Scale (see GSRS:Digestive Diseases and Sciences, 1988, Vol. 33, No. 2, pp. 129-134), disease-specific QOL related to IBS was measured based on IBS-quality of life (see IBS-QOL:Digestive Diseases and Sciences, 1998, Vol. 43, No. 2, pp. 400-411), general QOL was measured based on Medical Outcome Study 36-item Short Form Health Survey (see SF-36: Journal of Clinical Epidemiology, 1998, Vol. 51, pp. 1045-53), anxiety was measured based on State Trait Anxiety Inventory (see STAI: Perceptual and motor skills, Vol. 69, pp. 611-617), depression was measured based on Self-rating Depression Scale (see SDS: Biopsychosocial Medicine, 2008, Vol. 2, No. 20, and Zung WW: A Self-Rating Depression Scale. Arch Gen Psychiatry 1965, 12:63-70) and subjective stress was measured based on Perceived Stress Scale (see PSS: PLOS one, 2012, Vol. 7, No. 9, e42450, and Cohen S, Kamarck T, Mermelstein R (1983) A global measure of perceived stress. J Health Soc Behav 24: pp. 385-396). Next, times of bowel motion, stomachache, and the like, were recorded in a symptom diary for both IBS patients and healthy individuals, and IBS symptom and subjective stress were quantified for 28 days. As for the IBS symptoms, each of stomachache, abdominal discomfort, abdominal distension, feel of residual stool, feeling of urgent need to defecate, and straining at stool was evaluated as an ordinate scale from 1 to 7, types of stools from 1 to 7 based on Bristol Stool Form Scale (see Gastroenterology, 1997, Vol. 32, No. 9, pp. 920-924), and defecation frequency was evaluated as a real number. The subjective stress was evaluated based on an ordinate scale from 1 to 7. On the medium symptom aggravation day or invariant day, IBS-SI and PSS were reexamined. In addition, on the final day, IBS-SI, SIBSQ, GSRS, IBS-QOL, SF-36, STAI, SDS, and PSS negative morbidity were measured. IBS patients and healthy individuals were compared in terms of each evaluation item.

[Results] In IBS patients, IBS-SI, SIBSQ, GSRS, IBS-QOL, SF-36, SDS, and STAI of the base value were significantly higher ($p<0.01$), and stomachache was also significantly higher ($p<0.01$) as compared with those in healthy individuals.

(8) Metabolome analysis

Chromatogram data obtained by an LC/MS (4000QTRAP) analysis specified a metabolite observed in human urine using LC/MS/MS data analysis software "Analyst 1.4.2" (manufactured by AB SCIEX), and calculated a peak area value or peak intensity. Then, from these data, information of a mass number of each metabolite peak, elution time, a peak area value, peak intensity value, and a metabolite name were extracted using Office Excel 2007 (Microsoft).

Chromatogram data obtained by an LC/MS (LCT Premier) analysis were converted into reading data using 2DICAL (MITSUI KNOWLEDGE INDUSTRY CO., LTD.), and all data were subjected to peak alignment. Furthermore, based on the information on each measurement polarity mode (positive and negative), accurate mass number, and elution time, metabolite peak was identified. Then, from these data, accurate mass number, elution time, peak area value, and peak intensity value of each metabolite peak was extracted using Office Excel 2007 (Microsoft).

Data obtained from the above-mentioned two types of MS machines were input into Array analysis software "Expressionist Pro Analyst Ver. 5.1.4" (Genedata) and Office Excel 2007, respectively, and the variation ratio of peak area value to peak intensity value and the p-value of each metabolite were calculated between healthy individuals and IBS patients.

(9) Statistical analysis

The above obtained data were analyzed using statistical analysis software, SPSS version21 (IBM). Statistics were subjected to Welch's t-test between all healthy individuals and all IBS patients, and between healthy individuals and IBS patients for each of male and female subjects, or the like. Peaks showing a p-value of less than 0.2 and variation range of signal values in both groups of 1.5-fold or more or 0.67-fold or less were considered as biomarker candidates, and 102 peaks were screened and selected. Generalized Estimating Equation (GEE) was applied to the obtained 102 peaks. Then, significant peaks which satisfied $p<0.05$ in both the between-group difference or the between subgroup variation–time variation interaction were extracted.

IBS symptom was defined as dependent variable, and 44 peaks which were significant peaks in age, sex, PSS, drug, and Generalized Estimating Equation were defined as independent variable, and multiple regression analysis was carried out based on the stepwise method.

GEE (SPSS version21 (IBM)) was applied to the 102 peaks obtained in the statistical analysis together with the quinolinic acid/kynurenic acid ratio and quinolinic acid/xanthurenic acid ratio. Then, significant peaks and ratios which satisfied $p<0.05$ in both difference between groups or between subgroup variation–time variation interaction were extracted.

[Results]

Figure 2:
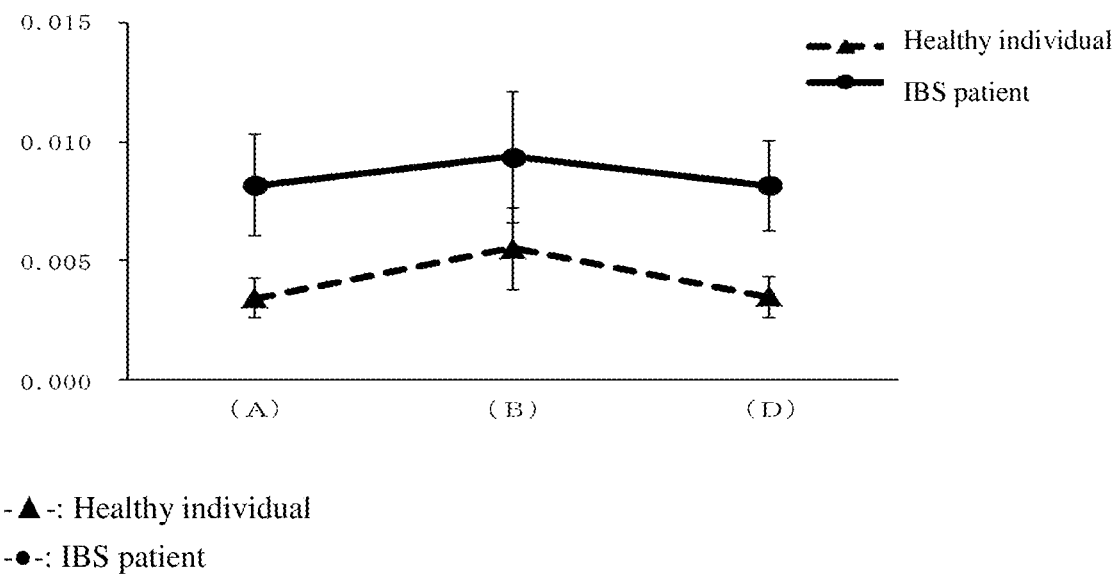
FIG. 2 shows results of comparison of a quinolinic acid/kynurenic acid ratio between healthy individuals and IBS patients. The ordinate shows a quinolinic acid/kynurenic acid ratio, and the abscissa shows urine collection points shown in Example 1 (4).

As a result, among well-known compounds as metabolite, as a biomarker of IBS, compounds shown in the below-mentioned Table 5 were found. Furthermore, change in the 29 types of biomarkers shown in Table 5 in IBS male patients and female patients are shown in Table 6. Furthermore, the change in quinolinic acid/kynurenic acid ratio and quinolinic acid/xanthurenic acid ratio were compared between healthy individuals and IBS patients, and the results are shown in FIGS. 1 and 2.

TABLE 5

| Compound No. | m/z value | Retention time (min) | Detection ion mode | Elemental composition | Compound name |
| --- | --- | --- | --- | --- | --- |
| 1 | 159.1830 | 2.6 | Positive | $C_7H_{13}NO_3$ | 2-methylbutyrylglycine |
| 2 | 368.4880 | 4.8 | Negative | $C_{19}H_{28}O_5S$ | DHEAS |
| 3 | 368.4700 | 4.8 | Negative | $C_{20}H_{32}O_6$ | 11-dehydro TXB2 |
| 4 | 350.4290 | 4.4 | Negative | $C_{18}H_{22}O_5S$ | Estrone sulfate |
| 5 | 264.3169 | 3.9 | Negative | $C_{15}H_{20}O_4$ | gamma-CEHC |
| 6 | 251.2500 | 1.6 | Negative | $C_{10}H_{13}N_5O_3$ | 2'-Deoxyadenosine |
| 7 | 283.2410 | 1.7 | Negative | $C_{10}H_{13}N_5O_5$ | Guanosine |
| 8 | 267.2500 | 1.7 | Negative | $C_{10}H_{13}N_5O_4$ | 2'-Deoxyguanosine |
| 9 | 268.2300 | 1.6 | Negative | $C_{10}H_{12}N_4O_5$ | Inosine |
| 10 | 205.1700 | 2.6 | Positive | $C_{10}H_7NO_4$ | Xanthurenic acid |
| 11 | 189.1680 | 2.7 | Positive | $C_{10}H_7NO_3$ | Kynurenic acid |
| 12 | 356.5000 | 4.4 | Negative | $C_{20}H_{36}O_5$ | 8-Iso prostaglandin F1α |
| 13 | 356.5000 | 4.7 | Negative | $C_{20}H_{36}O_5$ | Prostaglandin F1α |
| 14 | 358.5000 | 5.2 | Positive | $C_{20}H_{38}O_5$ | 13,14-Dihydro prostaglandin F1α |
| 15 | 326.4000 | 4.1 | Negative | $C_{18}H_{30}O_5$ | 2,3-Dinor-11β-prostaglandin F2α |
| 16 | 352.5000 | 5.1 | Positive | $C_{20}H_{32}O_5$ | 13,14-Dihydro-15-keto prostaglandin D2 |
| 17 | 328.4000 | 3.1 | Positive | $C_{16}H_{24}O_7$ | Tetranor-prostaglandin DM |
| 18 | 366.4500 | 4.4 | Negative | $C_{20}H_{30}O_6$ | 11-Dehydro thromboxane B3 |
| 19 | 344.4000 | 3.8 | Negative | $C_{18}H_{32}O_6$ | 2,3-Dinor thromboxane B1 |
| 20 | 370.4800 | 5.0 | Positive | $C_{20}H_{34}O_6$ | Thromboxane B2 |
| 21 | 166.0219 | 0.6 | Negative | $C_7H_5NO_4$ | Quinolinic acid |
| 22 | 149.0450 | 0.7 | Negative | $C_5H_{10}O_5$ | Xylose |
| 23 | 325.2015 | 4.1 | Negative | $C_{18}H_{30}O_5$ | 2,3-Dinor -8-iso prostaglandin F2α |
| 24 | 152.0110 | 1.6 | Negative | $C_7H_5O_4$ | Gentisic acid |
| 25 | 133.0613 | 0.7 | Negative | $C_4H_8N_2O_3$ | Glycylglycine |
| 26 | 217.1301 | 1.0 | Positive | $C_8H_{16}N_4O_3$ | N-acetylarginine |
| 27 | 168.1025 | 1.7 | Positive | $C_9H_{13}NO_2$ | 3-Methoxytyramine |
| 28 | 181.0501 | 1.0 | Negative | $C_9H_{10}O_4$ | Homovanillic acid |
| 29 | 197.0450 | 1.7 | Negative | $C_9H_{10}O_5$ | Vanillylmandelic acid |

TABLE 6

| Compound No. | Male IBS patient | Female IBS patient |
| --- | --- | --- |
| 1 | Increase | Increase |
| 2 | Decrease | Decrease |
| 3 | Decrease | Decrease |
| 4 | Decrease | Increase |
| 5 | Decrease | — |
| 6 | Increase | Increase |

TABLE 6-continued

| Compound No. | Male IBS patient | Female IBS patient |
| --- | --- | --- |
| 7 | Increase | Increase |
| 8 | Increase | Increase |
| 9 | — | Increase |
| 10 | Decrease | — |
| 11 | Decrease | — |
| 12 | Increase | Increase |
| 13 | Increase | Increase |
| 14 | — | Increase |
| 15 | Increase | Increase |
| 16 | Increase | Increase |
| 17 | Increase | Increase |
| 18 | — | Increase |
| 19 | — | Increase |
| 20 | — | Increase |
| 21 | Increase | — |
| 22 | Increase | Increase |
| 23 | Increase | — |
| 24 | Decrease | Decrease |
| 25 | — | Decrease |
| 26 | Increase | Increase |
| 27 | Increase | Increase |
| 28 | Decrease | Decrease |
| 29 | Decrease | Decrease |

Furthermore, as biomarkers for IBS, a total of 82 types of compounds having unknown structures were found as shown in the following Tables 7, 8, and 9. The change in the 82 types biomarkers shown in Tables 7, 8, and 9 in IBS male patients and female patients, are shown in Tables 10, 11, and 12. Note here that elemental compositions in Tables 7 to 9 were candidate composition formulae estimated from MS measurement values indicated by data analysis software.

TABLE 7

| Compound No. | m/z value | Detection ion mode | Retention time (min) | Elemental composition | Compound name estimated from composition formula |
| --- | --- | --- | --- | --- | --- |
| (1) | 181.2360 | Positive | 2.4 | $C_{12}H_{23}N$ or $C_{11}H_{19}NO$ | |
| (2) | 325.1638 | Positive | 4.2 | Plurality | |
| (3) | 364.0699 | Positive | 1.8 | Plurality | |
| (4) | 280.0994 | Positive | 3.1 | Plurality | |
| (5) | 562.2519 | Positive | 4.0 | Plurality | |
| (6) | 392.0800 | Positive | 2.4 | $C_{18}H_{16}O_{10}$ or $C_{11}H_{21}O_{13}P$ | |
| (7) | 180.7781 | Positive | 2.4 | — | |
| (8) | 212.0891 | Positive | 2.2 | Plurality | |
| (9) | 198.0746 | Positive | 1.3 | Plurality | |
| (10) | 469.2663 | Positive | 5.1 | $C_{24}H_{39}NO_8$ | |
| (11) | 320.0570 | Positive | 2.6 | $C_{15}H_{12}O_8$ | |
| (12) | 216.1003 | Positive | 1.9 | $C_{10}H_{16}O_5$ or $C_9H_{16}N_2O_2S$ | |
| (13) | 226.3766 | Positive | 1.6 | — | |
| (14) | 248.0630 | Positive | 4.1 | $C_{12}H_{12}N_2O_2S$ | |
| (15) | 247.4804 | Positive | 4.7 | — | |
| (16) | 345.2490 | Positive | 4.7 | $C_{18}H_{35}NO_5$ | |
| (17) | 562.2139 | Positive | 4.5 | Plurality | |
| (18) | 182.3232 | Positive | 1.8 | — | |
| (19) | 298.1211 | Positive | 3.8 | Plurality | |
| (20) | 558.2173 | Positive | 2.8 | Plurality | |
| (21) | 301.5775 | Positive | 4.4 | — | |
| (22) | 221.3823 | Positive | 1.7 | — | |
| (23) | 156.0772 | Positive | 2.3 | $C_8H_{12}O_3$ or $C_{10}H_8N_2$ | |
| (24) | 300.4930 | Positive | 2.5 | — | |
| (25) | 169.3047 | Positive | 2.1 | — | |
| (26) | 504.1944 | Positive | 4.1 | $C_{26}H_{32}O_{10}$ or $C_{22}H_{30}Cl_2N_{10}$ | |
| (27) | 458.1049 | Positive | 2.4 | $C_{19}H_{22}O_{13}$ or $C_{26}H_{18}O_8$ | 2,4,6-Trihydroxybenzoic acid |

\* "Plurality" in Table denotes a plurality of elemental compositions.

TABLE 8

| Compound No. | m/z value | Detection ion mode | Retention time (min) | Elemental composition | Compound name estimated from composition formula |
| --- | --- | --- | --- | --- | --- |
| (28) | 283.0484 | Positive | 2.2 | $C_{12}H_{13}NO_5S$ | |
| (29) | 325.5613 | Positive | 4.2 | — | |
| (30) | 280.1037 | Positive | 2.2 | Plurality | |
| (31) | 313.5927 | Positive | 4.5 | — | |
| (32) | 175.0626 | Positive | 2.0 | $C_{10}H_9NO_2$ or $C_5H_9N_3O_4$ | |

TABLE 8-continued

| Compound No. | m/z value | Detection ion mode | Retention time (min) | Elemental composition | Compound name estimated from composition formula |
|---|---|---|---|---|---|
| (33) | 226.1345 | Positive | 2.6 | $C_{16}H_{18}O$ or $C_{11}H_{18}N_2O_3$ | |
| (34) | 406.0908 | Positive | 2.7 | Plurality | |
| (35) | 406.0840 | Positive | 2.2 | Plurality | |
| (36) | 170.0573 | Positive | 2.5 | $C_7H_{10}N_2OS$ or $C_8H_{10}O_4$ | |
| (37) | 295.1404 | Positive | 2.3 | $C_{18}H_{18}FN_3$ or $C_{15}H_{21}NO_5$ | |
| (38) | 381.2543 | Positive | 4.8 | $C_{21}H_{35}NO_5$ or $C_{18}H_{40}NO_5P$ | Sphinganine 1-phosphate |
| (39) | 271.1637 | Positive | 4.7 | $C_{17}H_{21}NO_2$ | |
| (40) | 474.1510 | Positive | 3.8 | $C_{31}H_{22}O_5$ or $C_{25}H_{27}ClO_7$ | |
| (41) | 424.1398 | Positive | 4.3 | Plurality | |
| (42) | 299.0496 | Positive | 1.8 | $C_{18}H_9NO_6$ | |
| (43) | 244.4071 | Positive | 3.5 | — | |
| (44) | 121.0887 | Positive | 1.5 | $C_8H_{11}N$ | |
| (45) | 327.2469 | Positive | 4.8 | $C_{17}H_{33}N_3O_3$ or $C_{22}H_{33}NO$ | |
| (46) | 503.2722 | Positive | 4.6 | Plurality | |
| (47) | 286.1600 | Positive | 2.5 | Plurality | |
| (48) | 292.5018 | Positive | 4.0 | — | |
| (49) | 420.1101 | Positive | 2.7 | Plurality | |
| (50) | 430.0742 | Positive | 1.8 | $C_{11}H_{20}N_4O_{10}P_2$ | CMP-2-aminoethyl-phosphonate |
| (51) | 284.1745 | Positive | 3.6 | Plurality | |
| (52) | 291.1521 | Positive | 2.1 | Plurality | |
| (53) | 462.0711 | Positive | 1.8 | Plurality | |
| (54) | 388.2160 | Positive | 3.8 | Plurality | |
| (55) | 260.0827 | Positive | 2.4 | Plurality | |

\* "Plurality" in Table denotes a plurality of elemental compositions.

TABLE 9

| Compound No. | m/z value | Detection ion mode | Retention time (min) | Elemental composition | Compound name estimated from composition formula |
|---|---|---|---|---|---|
| (56) | 259.1837 | Positive | 4.0 | $C_{13}H_{25}NO_4$ | |
| (57) | 302.7432 | Positive | 4.4 | — | |
| (58) | 526.2485 | Positive | 3.3 | $C_{26}H_{38}O_{11}$ or $C_{30}H_{38}O_8$ | |
| (59) | 419.8702 | Positive | 0.6 | — | |
| (60) | 446.0974 | Positive | 4.2 | $C_{18}H_{22}O_{11}S$ | |
| (61) | 537.1957 | Positive | 2.9 | $C_{29}H_{31}NO_9$ | |
| (62) | 601.2663 | Positive | 2.5 | $C_{29}H_{39}N_5O_7S$ | |
| (63) | 444.1750 | Positive | 3.9 | $C_{24}H_{28}O_8$ or $C_{26}H_{24}N_2O_5$ | |
| (64) | 192.0298 | Positive | 0.6 | $C_6H_8O_7$ or $C_{10}H_8O_2S$ | |
| (65) | 346.1793 | Positive | 3.8 | Plurality | |
| (66) | 182.0914 | Positive | 0.7 | Plurality | |
| (67) | 205.1084 | Positive | 0.9 | $C_{12}H_{15}NO_2$ or $C_{11}H_{12}FN_3$ | |
| (68) | 344.1737 | Positive | 4.2 | Plurality | |
| (69) | 296.1592 | Positive | 2.6 | Plurality | |
| (70) | 361.2379 | Positive | 4.4 | Plurality | |
| (71) | 162.0990 | Positive | 1.5 | $C_6H_{14}N_2O_3$ or $C_{11}H_{14}O$ | |
| (72) | 196.2382 | Positive | 0.6 | $C_{14}H_{28}$ | |
| (73) | 292.0330 | Positive | 0.7 | Plurality | |
| (74) | 130.0713 | Positive | 2.2 | $C_5H_{10}N_2O_2$ or $C_6H_{10}O_3$ | |
| (75) | 389.2738 | Positive | 5.0 | Plurality | |
| (76) | 340.0995 | Positive | 2.1 | Plurality | |
| (77) | 402.2212 | Positive | 4.3 | Plurality | |
| (78) | 210.0532 | Positive | 0.7 | Plurality | |
| (79) | 306.0155 | Positive | 0.7 | $C_9H_{11}N_2O_8P$ | 2'3'-Cyclic UMP |
| (80) | 260.1539 | Positive | 1.8 | Plurality | |

TABLE 9-continued

| Compound No. | m/z value | Detection ion mode | Retention time (min) | Elemental composition | Compound name estimated from composition formula |
|---|---|---|---|---|---|
| (81) | 342.0708 | Positive | 1.2 | Plurality | |
| (82) | 130.0348 | Positive | 0.8 | $C_9H_6O$ or $C_5H_6O_4$ | |

* "Plurality" in Table denotes a plurality of elemental compositions.

TABLE 10

| Compound No. | Male IBS patient | Female IBS patient |
|---|---|---|
| (1) | Increase | Increase |
| (2) | Increase | Increase |
| (3) | Increase | — |
| (4) | Increase | Increase |
| (5) | Increase | Increase |
| (6) | Increase | — |
| (7) | Increase | Increase |
| (8) | Increase | — |
| (9) | Increase | Increase |
| (10) | — | Increase |
| (11) | — | Increase |
| (12) | Increase | Increase |
| (13) | Increase | Increase |
| (14) | Increase | Increase |
| (15) | Increase | Increase |
| (16) | Increase | Increase |
| (17) | Increase | — |
| (18) | Increase | — |
| (19) | Increase | Increase |
| (20) | Increase | Increase |
| (21) | Increase | Increase |
| (22) | Increase | Increase |
| (23) | — | Increase |
| (24) | Increase | Increase |
| (25) | Increase | Increase |
| (26) | Increase | Increase |
| (27) | Increase | Increase |

TABLE 11

| Compound No. | Male IBS patient | Female IBS patient |
|---|---|---|
| (28) | — | Increase |
| (29) | Increase | Increase |
| (30) | — | Increase |
| (31) | Increase | Increase |
| (32) | Increase | Increase |
| (33) | Increase | Increase |
| (34) | Increase | Increase |
| (35) | Increase | Increase |
| (36) | Increase | Increase |
| (37) | — | Increase |
| (38) | Increase | Increase |
| (39) | Increase | Increase |
| (40) | Increase | Increase |
| (41) | Increase | — |
| (42) | Increase | Increase |
| (43) | Increase | Increase |
| (44) | Increase | Increase |
| (45) | Increase | Increase |
| (46) | Increase | Increase |
| (47) | Increase | Increase |
| (48) | Increase | — |
| (49) | Increase | Increase |
| (50) | Increase | Increase |
| (51) | Increase | — |
| (52) | Increase | — |
| (53) | Increase | — |
| (54) | Increase | Increase |
| (55) | Increase | Decrease |

TABLE 12

| Compound No. | Male IBS patient | Female IBS patient |
|---|---|---|
| (56) | Increase | Increase |
| (57) | Increase | Increase |
| (58) | Increase | Increase |
| (59) | Decrease | Decrease |
| (60) | Decrease | Decrease |
| (61) | Decrease | Decrease |
| (62) | Increase | Increase |
| (63) | Increase | — |
| (64) | Increase | Increase |
| (65) | Increase | Increase |
| (66) | Increase | Increase |
| (67) | Increase | Increase |
| (68) | Increase | Increase |
| (69) | Decrease | Decrease |
| (70) | — | Decrease |
| (71) | Increase | Increase |
| (72) | — | Increase |
| (73) | Increase | Increase |
| (74) | Increase | Increase |
| (75) | Decrease | Decrease |
| (76) | Decrease | Decrease |
| (77) | Decrease | Decrease |
| (78) | Increase | Increase |
| (79) | Increase | Increase |
| (80) | Decrease | Decrease |
| (81) | Decrease | Decrease |
| (82) | Increase | Increase |

INDUSTRIAL APPLICABILITY

A biomarker of the present invention enables diagnosis of IBS to be carried out in a noninvasive and convenient method rapidly and accurately. Furthermore, the present invention can provide biomarkers useful for determination of the presence or absence of morbidity of IBS, determination of severity of IBS, determination of types of IBS, determination of necessity of treatment of IBS, and confirmation of drug efficacy of an IBS therapeutic agent. Furthermore, the present invention can provide a screening method in drug development of IBS therapeutic agents, a method for screening and selecting a therapeutic agent suitable for an IBS patient, a diagnosis drug for IBS, a kit for diagnosis of IBS, and a method for diagnosing IBS.

The invention claimed is:

1. A method for screening and selecting a therapeutic agent for treating irritable bowel syndrome, the method comprising the following steps in order,
    obtaining a first urine sample of a irritable bowel syndrome patient, measuring a concentration of a biomarker in the first urine sample, administering a candidate therapeutic agent to the patient,
    obtaining a second urine sample of the patient after the administration of the candidate therapeutic agent to the patient,
    measuring a concentration of the biomarker in the second urine sample under the same conditions for measuring the concentration of the biomarker in the first urine sample, and selecting the candidate therapeutic agent as the therapeutic agent for irritable bowel syndrome:
  when the concentration of the biomarker in the first urine sample of the patient is greater than the concentration of the biomarker in the second urine sample,
wherein the biomarker is selected from the group consisting of compounds whose m/z value and retention time, measured by LC/MS, are:
(1) 251.3 and 1.6 min- Compound No. 6, 283.2 and 1.7 min- Compound No. 7, 267.3 and 1.7 min- Compound No. 8, 268.2 and 1.6 min- Compound No. 9, 356.5 and 4.4 min- Compound No. 12, 356.5 and 4.7 min- Compound No. 13, 358.5 and 5.2 min- Compound No. 14, 326.4 and 4.1 min- Compound No. 15, 352.5 and 5.1 min- Compound No. 16, 328.4 and 3.1 min- Compound No. 17, 366.5 and 4.4 min- Compound No. 18, 344.4 and 3.8 min- Compound No. 19, 370.5 and 5.0 min- Compound No. 20, 166.0 and 0.6 min- Compound No. 21, 149.0 and 0.7 min- Compound No. 22, 325.2 and 4.1 min- Compound No. 23, 217.1 and 1.0 min- Compound No. 26, 168.1 and 1.7 min- Compound No. 27,
wherein the measuring is performed by LC/MS equipped with ACQUITY UPLC BEH C18 (1.7 μm, 2.1 mm×150 mm; manufactured by Waters) as an LC column and 4000QTRAP (manufactured by AB SCIEX) as an MS machine, and
wherein the m/z value contains an error range of ±0.1 and the retention time contains an error range of ±0.1 min, and wherein the urine sample is processed to form 250 μL of supernatant of the urine sample, which is centrifuged at 2500 rpm for 15 min at 4° C. by a centrifugal machine, is mixed with 750 μL of 0.1% (w/w) formic acid aqueous solution to which 0.09% (w/w) sodium azide has been added to obtain a mixed solution, and the mixed solution is measured under a condition of
a column temperature is 40° C.;
an automatic sampler temperature is 4° C.;
an injection amount of measuring sample is 5 μL;
a flow rate is 0.30 mL/min;
analysis time is 21 min; and
gradient conditions (A/B (v/v %)) of a mobile phase (A) 0.1% (w/w) formic acid aqueous solution and a mobile phase (B) acetonitrile are 0-7 min (100/0), 7-14 min (0/100), and 14-21 min (100/0), and
(2) 198.1 and 1.3 min- Compound No. 9a, 121.1 and 1.5 min- Compound No. 44a, 226.4 and 1.6 min- Compound No. 13a, 221.4 and 1.7 min- Compound No. 22a, 182.3 and 1.8 min- Compound No. 18a, 299.0 and 1.8 min- Compound No. 42a, 364.1 and 1.8 min- Compound No. 3a, 430.1 and 1.8 min- Compound No. 50a, 462.1 and 1.8 min- Compound No. 53a, 216.1 and 1.9 min- Compound No. 12a, 175.1 and 2.0 min- Compound No. 32a, 169.3 and 2.1 min- Compound No. 25a, 291.2 and 2.1 min- Compound No. 52a, 212.1 and 2.2 min- Compound No. 8a, 280.1 and 2.2 min- Compound No. 30a, 283.0 and 2.2 min- Compound No. 28a, 406.1 and 2.2 min- Compound No. 35a, 156.1 and 2.3 min- Compound No. 23a, 295.1 and 2.3 min- Compound No. 37a, 180.8 and 2.4 min- Compound No. 7a, 181.2 and 2.4 min- Compound No. 1a, 392.1 and 2.4 min- Compound No. 6a, 458.1 and 2.4 min- Compound No. 27a, 170.1 and 2.5 min- Compound No. 36a, 286.2 and 2.5 min- Compound No. 47a, 300.5 and 2.5 min- Compound No. 24a, 601.3 and 2.5 min- Compound No. 62a, 159.2 and 2.6 min- Compound No. 1, 226.1 and 2.6 min- Compound No. 33a, 320.1 and 2.6 min- Compound No. 11a, 406.1 and 2.7 min- Compound No. 34a, 420.1 and 2.7 min- Compound No. 49a, 558.2 and 2.8 min- Compound No. 20a, 280.1 and 3.1 min- Compound No. 4a, 526.2 and 3.3 min- Compound No. 58a, 244.4 and 3.5 min- Compound No. 43a, 284.2 and 3.6 min- Compound No. 51a, 298.1 and 3.8 min- Compound No. 19a, 388.2 and 3.8 min- Compound No. 54a, 474.2 and 3.8 min- Compound No. 40a, 444.2 and 3.9 min- Compound No. 63a, 259.2 and 4.0 min- Compound No. 56a, 292.5 and 4.0 min- Compound No. 48a, 562.3 and 4.0 min- Compound No. 5a, 248.1 and 4.1 min- Compound No. 14a, 504.2 and 4.1 min- Compound No. 26a, 325.2 and 4.2 min- Compound No. 2a, 325.6 and 4.2 min- Compound No. 29a, 424.1 and 4.3 min- Compound No. 41a, 301.6 and 4.4 min- Compound No. 21a, 302.7 and 4.4 min- Compound No. 57a, 313.6 and 4.5 min- Compound No. 31a, 562.2 and 4.5 min- Compound No. 17a, 503.3 and 4.6 min- Compound No. 46a, 247.5 and 4.7 min- Compound No. 15a, 271.2 and 4.7 min- Compound No. 39a, 345.3 and 4.7 min- Compound No. 16a, 327.2 and 4.8 min- Compound No. 45a, 381.3 and 4.8 min- Compound No. 38a, or 469.3 and 5.1 min- Compound No. 10a,
wherein the measuring is performed by LC/MS equipped with ACQUITY UPLC BEH C18 (1.7 μm, 2.1 mm×100 mm; manufactured by Waters) as the LC column and LCT Premier (manufactured by Waters) as the MS machine, and
wherein the m/z value contains an error range of ±0.1, and the retention time contains an error range of ±0.1 min, and wherein the urine sample is processed to form 250 μL of supernatant of the urine sample, which has been centrifuged at 2500 rpm for 15 min at 4° C. by a centrifugal machine, is mixed with 750 μL of 0.1% (w/w) formic acid aqueous solution to which 0.09% (w/w) sodium azide has been added to obtain a mixed solution, and the mixed solution is measured under a condition of
a column temperature is 40° C.;
an automatic sampler temperature is 4° C.;
an injection amount of measuring sample is 5 μL;
a flow rate is 0.30 mL/min;
analysis time is 17 min; and
gradient conditions (A/B (v/v %)) of a mobile phase (A) 0.1% (w/w) formic acid aqueous solution, and a mobile phase (B) 0.1% (w/w) formic acid methanol solution are 0-4 min (100/0), 4-4.5 min (30/70), 4.5-10 min (2/98), and 10-17 min (100/0), and
(3) 192.0 and 0.6 min- Compound No. 64a, 196.2 and 0.6 min- Compound No. 72a, 182.1 and 0.7 min- Compound No. 66a, 210.1 and 0.7 min- Compound No. 78a, 292.0 and 0.7 min- Compound No. 73a, 306.0 and 0.7 min- Compound No. 79a, 130.0 and 0.8 min- Compound No. 82a, 205.1 and 0.9 min- Compound No. 67a, 162.1 and 1.5 min- Compound No. 71a, 130.1 and 2.2 min- Compound No. 74a, 346.2 and 3.8 min- Compound No. 65a, 344.2 and 4.2 min- Compound No. 68a,
wherein the measuring is performed by LC/MS equipped with ACQUITY UPLC BEH C18 (1.7 μm, 2.1 mm×100 mm; manufactured by Waters) as the LC column and LCT Premier (manufactured by Waters) as the MS machine, and
wherein the m/z value contains an error range of ±0.1 and the retention time contains an error range of ±0.1 min, and wherein the urine sample is processed to form 250

µL of supernatant of the urine sample, which has been centrifuged at 2500 rpm for 15 min at 4° C. by a centrifugal machine, is mixed with 750 of 0.1% (w/w) formic acid aqueous solution to which 0.09% (w/w) sodium azide has been added to obtain a mixed solution, and the mixed solution is measured under a condition of a column temperature is 40° C.;
an automatic sampler temperature is 4° C.;
an injection amount of measuring sample is 5 µL;
a flow rate is 0.30 mL/min;
analysis time is 17 min; and
gradient conditions (A/B (v/v %)) of a mobile phase (A) 6.5 mM aqueous solution of ammonium hydrogencarbonate and a mobile phase (B) 6.5 mM aqueous solution of ammonium hydrogencarbonate in 95% (w/v) methanol are 0-4 min (100/0), 4-4.5 min (30/70), 4.5-10 min (2/98), and 10-17 min (100/0).

2. The method according to claim 1, wherein the biomarker is selected from the group consisting of 2-methylbutyrylglycine (Compound No. 1), 2'-deoxyadenosine (Compound No. 6), guanosine (Compound No. 7), 2'-deoxyguanosine (Compound No. 8), inosine (Compound No. 9), 8-iso-prostaglandin F1α (Compound No. 12), prostaglandin F1α (Compound No. 13), 13,14-dihydro-prostaglandin F1α (Compound No. 14), 2,3-dinor-11β-prostaglandin F2α (Compound No. 15), 13,14-dihydro-15-keto-prostaglandin D2 (Compound No. 16), tetranor-prostaglandin D metabolite (Compound No. 17), 11-dehydro-thromboxane B3 (Compound No. 18), 2,3-dinor-thromboxane B1 (Compound No. 19), thromboxane B2 (Compound No. 20), quinolinic acid (Compound No. 21), xylose (Compound No. 22), 2,3-dinor-8-iso-prostaglandin F2α (Compound No. 23), N-acetylarginine (Compound No. 26), and 3-methoxytyramine (Compound No. 27).

3. A method for diagnosing and treating irritable bowel syndrome in a subject, the method comprising:
(i) a step of diagnosing the subject with irritable bowel syndrome by obtaining a urine sample of the subject, measuring a concentration of a biomarker in the urine sample of the subject, and comparing the concentration with that of a healthy individual,
wherein the subject is diagnosed with irritable bowel syndrome when the concentration of the biomarker in the urine sample of the subject is greater than that of the healthy individual, and
(ii) a step of administering a therapeutic agent for treating irritable bowel syndrome to the diagnosed subject,
wherein the biomarker is selected from the group consisting of compounds whose m/z value and retention time, measured by LC/MS, are:
(1) 251.3 and 1.6 min- Compound No. 6, 283.2 and 1.7 min- Compound No. 7, 267.3 and 1.7 min- Compound No. 8, 268.2 and 1.6 min- Compound No. 9, 356.5 and 4.4 min- Compound No. 12, 356.5 and 4.7 min- Compound No. 13, 358.5 and 5.2 min- Compound No. 14, 326.4 and 4.1 min- Compound No. 15, 352.5 and 5.1 min- Compound No. 16, 328.4 and 3.1 min- Compound No. 17, 366.5 and 4.4 min- Compound No. 18, 344.4 and 3.8 min- Compound No. 19, 370.5 and 5.0 min- Compound No. 20, 166.0 and 0.6 min- Compound No. 21, 149.0 and 0.7 min- Compound No. 22, 325.2 and 4.1 min- Compound No. 23, 217.1 and 1.0 min- Compound No. 26, 168.1 and 1.7 min- Compound No. 27, wherein the measuring is performed by LC/MS equipped with ACQUITY UPLC BEH C18 (1.7 µm, 2.1 mm×150 mm; manufactured by Waters) as an LC column and 4000QTRAP (manufactured by AB SCIEX) as an MS machine, and wherein the m/z value contains an error range of ±0.1 and the retention time contains an error range of ±0.1 min, and wherein the urine sample is processed to form 250 µL of supernatant of the urine sample, which has been centrifuged at 2500 rpm for 15 min at 4° C. by a centrifugal machine, is mixed with 750 µL of 0.1% (w/w) formic acid aqueous solution to which 0.09% (w/w) sodium azide has been added to obtain a mixed solution, and the mixed solution is measured under a condition of a column temperature is 40° C.;
an automatic sampler temperature is 4° C.;
an injection amount of measuring sample is 5 µL;
a flow rate is 0.30 mL/min;
analysis time is 21 min; and
gradient conditions (A/B (v/v %)) of a mobile phase (A) 0.1% (w/w) formic acid aqueous solution and a mobile phase (B) acetonitrile are 0-7 min (100/0), 7-14 min (0/100), and 14-21 min (100/0), and (2) 198.1 and 1.3 min- Compound No. 9a, 121.1 and 1.5 min- Compound No. 44a, 226.4 and 1.6 min- Compound No. 13a, 221.4 and 1.7 min- Compound No. 22a, 182.3 and 1.8 min- Compound No. 18a, 299.0 and 1.8 min- Compound No. 42a, 364.1 and 1.8 min- Compound No. 3a, 430.1 and 1.8 min- Compound No. 50a, 462.1 and 1.8 min- Compound No. 53a, 216.1 and 1.9 min- Compound No. 12a, 175.1 and 2.0 min- Compound No. 32a, 169.3 and 2.1 min- Compound No. 25a, 291.2 and 2.1 min- Compound No. 52a, 212.1 and 2.2 min- Compound No. 8a, 280.1 and 2.2 min- Compound No. 30a, 283.0 and 2.2 min- Compound No. 28a, 406.1 and 2.2 min- Compound No. 35a, 156.1 and 2.3 min- Compound No. 23a, 295.1 and 2.3 min- Compound No. 37a, 180.8 and 2.4 min- Compound No. 7a, 181.2 and 2.4 min- Compound No. 1a, 392.1 and 2.4 min- Compound No. 6a, 458.1 and 2.4 min- Compound No.27a, 170.1 and 2.5 min- Compound No. 36a, 286.2 and 2.5 min- Compound No. 47a, 300.5 and 2.5 min- Compound No. 24a, 601.3 and 2.5 min- Compound No. 62a, 159.2 and 2.6 min- Compound No. 1, 226.1 and 2.6 min- Compound No. 33a, 320.1 and 2.6 min- Compound No. 11a, 406.1 and 2.7 min- Compound No. 34a, 420.1 and 2.7 min- Compound No. 49a, 558.2 and 2.8 min- Compound No. 20a, 280.1 and 3.1 min- Compound No. 4a, 526.2 and 3.3 min- Compound No. 58a, 244.4 and 3.5 min- Compound No. 43a, 284.2 and 3.6 min- Compound No. 51a, 298.1 and 3.8 min- Compound No. 19a, 388.2 and 3.8 min- Compound No. 54a, 474.2 and 3.8 min- Compound No. 40a, 444.2 and 3.9 min- Compound No. 63a, 259.2 and 4.0 min- Compound No. 56a, 292.5 and 4.0 min- Compound No. 48a, 562.3 and 4.0 min- Compound No. 5a, 248.1 and 4.1 min- Compound No. 14a, 504.2 and 4.1 min- Compound No. 26a, 325.2 and 4.2 min- Compound No. 2a, 325.6 and 4.2 min- Compound No. 29a, 424.1 and 4.3 min- Compound No. 41a, 301.6 and 4.4 min- Compound No. 21a, 302.7 and 4.4 min- Compound No. 57a, 313.6 and 4.5 min- Compound No. 31a, 562.2 and 4.5 min- Compound No. 17a, 503.3 and 4.6 min- Compound No. 46a, 247.5 and 4.7 min- Compound No. 15a, 271.2 and 4.7 min- Compound No. 39a, 345.3 and 4.7 min- Compound No. 16a, 327.2 and 4.8 min- Compound No. 45a, 381.3 and 4.8 min- Compound No. 38a, or 469.3 and 5.1 min- Compound No. 10a, wherein the measuring is performed by LC/MS equipped with ACQUITY UPLC BEH C18 (1.7 µm, 2.1 mm×100 mm; manufactured by Waters) as the LC column and LCT Premier (manufactured by Waters) as the MS machine, and wherein the m/z value contains an error range of ±0.1, and the retention time contains an error range of ±0.1 min, and wherein the urine sample is processed to form 250 µL of supernatant of the urine sample, which has been centrifuged at 2500 rpm for 15 min at 4° C. by a centrifugal machine, is mixed with 750 µL of 0.1% (w/w) formic acid aqueous solution to which 0.09% (w/w) sodium azide has been added to obtain a mixed solution, and the mixed solution is measured under a condition of a column temperature is 40° C.;
an automatic sampler temperature is 4° C.;
an injection amount of measuring sample is 5µL;
a flow rate is 0.30 mL/min;
analysis time is 17 min; and
gradient conditions (A/B (v/v %)) of a mobile phase (A) 0.1% (w/w) formic acid aqueous solution, and a mobile phase (B) 0.1% (w/w) formic acid methanol solution are 0-4 min (100/0), 4-4.5 min (30/70), 4.5-10 min (2/98), and 10-17 min (100/0), and (3) 192.0 and 0.6 min- Compound No. 64a, 196.2 and 0.6 min- Compound No. 72a, 182.1 and 0.7 min- Compound No. 66a, 210.1 and 0.7 min- Compound No. 78a, 292.0 and 0.7 min- Compound No. 73a, 306.0 and 0.7 min- Compound No. 79a, 130.0 and 0.8 min- Compound No. 82a, 205.1 and 0.9 min- Compound No. 67a, 162.1 and 1.5 min- Compound No. 71a, 130.1 and 2.2 min- Compound No. 74a, 346.2 and 3.8 min- Compound No. 65a, 344.2 and 4.2 min- Compound No. 68a, wherein the measuring is performed by LC/MS equipped with ACQUITY UPLC BEH C18 (1.7 µm, 2.1 mm×100 mm; manufactured by Waters) as the LC column and LCT Premier (manufactured by Waters) as the MS machine, and wherein the m/z value contains an error range of ±0.1 and the retention time contains an error range of ±0.1 min, and wherein the urine sample is processed to form 250 µL of supernatant of the urine sample, which has been centrifuged at 2500 rpm for 15 min at 4° C. by a centrifugal machine, is mixed with 750 µL of 0.1% (w/w) formic acid aqueous solution to which 0.09% (w/w) sodium azide has been added to obtain a mixed solution, and the mixed solution is measured under a condition of a column temperature is 40° C.;
an automatic sampler temperature is 4° C.;
an injection amount of measuring sample is 5µL;
a flow rate is 0.30 mL/min;
analysis time is 17 min; and
gradient conditions (A/B (v/v %)) of a mobile phase (A) 6.5 mM aqueous solution of ammonium hydrogencarbonate and a mobile phase (B) 6.5 mM aqueous solution of ammonium hydrogencarbonate in 95% (w/v) methanol are 0-4 min (100/0), 4-4.5 min (30/70), 4.5-10 min (2/98), and 10-17 min (100/0).

4. The method according to claim 3, wherein the biomarker is selected from the group consisting of 2-methylbutyrylglycine (Compound No. 1), 2'-deoxyadenosine (Compound No. 6), guanosine (Compound No. 7), 2'-deoxyguanosine (Compound No. 8), inosine (Compound No. 9), 8-iso-prostaglandin F1α (Compound No. 12), prostaglandin F1α (Compound No. 13), 13,14-dihydro-prostaglandin F1α (Compound No. 14), 2,3-dinor-11β-prostaglandin F2α (Compound No. 15), 13,14-dihydro-15-keto-prostaglandin D2 (Compound No. 16), tetranor-prostaglandin D metabolite (Compound No. 17), 11-dehydro-thromboxane B3 (Compound No. 18), 2,3-dinor-thromboxane B1 (Compound No. 19), thromboxane B2 (Compound No. 20), quinolinic acid (Compound No. 21), xylose (Compound No. 22), 2,3-dinor-8-iso-prostaglandin F2α (Compound No. 23), N-acetylarginine (Compound No. 26), and 3-methoxytyramine (Compound No. 27).

5. The method according to claim 3, the step (i) further comprises calculating a ratio of the concentrations of any two or more types of biomarkers in the urine sample of the subject.

6. The method according to claim 5, wherein the calculating a ratio of the concentrations of any two or more types of biomarkers is calculating a quinolinic acid/xanthurenic acid ratio or a quinolinic acid/kynurenic acid ratio.

7. A method for screening and selecting a therapeutic agent for treating irritable bowel syndrome, the method comprising the following steps in order, obtaining a first urine sample of a irritable bowel syndrome patient, measuring a concentration of a biomarker in the first urine sample, administering a candidate therapeutic agent to the patient, obtaining a second urine sample of the patient after the administration of the candidate therapeutic agent to the patient, measuring a concentration of the biomarker in the second urine sample under the same conditions for measuring the concentration of the biomarker in the first urine sample, and selecting the candidate therapeutic agent as the therapeutic agent for irritable bowel syndrome when the concentration of the biomarker in the first urine sample of the patient is less than the concentration of the biomarker in the second urine sample, wherein the biomarker is selected from the group consisting of compounds whose m/z value and retention time, measured by LC/MS, are:

(1) 264.3 and 3.9 min- Compound No. 5, 205.2 and 2.6 min- Compound No. 10, 189.2 and 2.7 min- Compound No. 11, 152.0 and 1.6 min- Compound No. 24, 133.1 and 0.7 min- Compound No. 25, 181.1 and 1.0 min- Compound No. 28, or 197.0 and 1.7 min- Compound No. 29, wherein the measuring is performed by LC/MS equipped with ACQUITY UPLC BEH C18 (1.7 µm, 2.1 mm×150 mm; manufactured by Waters) as an LC column and 4000QTRAP (manufactured by AB SCIEX) as an MS machine, and wherein the m/z value contains an error range of ±0.1 and the retention time contains an error range of ±0.1 min, and wherein when the urine sample is processed to form 250 µL of supernatant of the urine sample, which has been centrifuged at 2500 rpm for 15 min at 4° C. by a centrifugal machine, is mixed with 750 µL of 0.1% (w/w) formic acid aqueous solution to which 0.09% (w/w) sodium azide has been added to obtain a mixed solution, and the mixed solution is measured under a
condition of a column temperature is 40° C.;

an automatic sampler temperature is 4° C.;

an injection amount of measuring sample is 5 μL;

a flow rate is 0.30 mL/min;

analysis time is 21 min; and gradient conditions (A/B (v/v %)) of a mobile phase (A) 0.1% (w/w) formic acid aqueous solution and a mobile phase (B) acetonitrile are 0-7 min (100/0), 7-14 min (0/100), and 14-21 min (100/0), and (2) 419.9 and 0.6 min- Compound No. 59a, 537.2 and 2.9 min- Compound No. 61a, or 446.1 and 4.2 min- Compound No. 60a, wherein the measuring is performed by LC/MS equipped with ACQUITY UPLC BEH C18 (1.7 μm, 2.1 mm×100 mm; manufactured by Waters) as the LC column and LCT Premier (manufactured by Waters) as the MS machine, and wherein the m/z value contains an error range of ±0.1, and the retention time contains an error range of ±0.1 min, and wherein the urine sample is processed to form 250 μL of supernatant of the urine sample, which has been centrifuged at 2500 rpm for 15 min at 4° C. by a centrifugal machine, is mixed with 750 μL of 0.1% (w/w) formic acid aqueous solution to which 0.09% (w/w) sodium azide has been added to obtain a mixed solution, and the mixed solution is measured under a condition of a column temperature is 40° C.;

an automatic sampler temperature is 4° C.;

an injection amount of measuring sample is 5μL;

a flow rate is 0.30 mL/min;

analysis time is 17 min; and gradient conditions (A/B (v/v %)) of a mobile phase (A) 0.1% (w/w) formic acid aqueous solution, and a mobile phase (B) 0.1% (w/w) formic acid methanol solution are 0-4 min (100/0), 4-4.5 min (30/70), 4.5-10 min (2/98), and 10-17 min (100/0), and (3) 342.1 and 1.2 min- Compound No. 81a, 260.2 and 1.8 min- Compound No. 80a, 340.1 and 2.1 min- Compound No. 76a, 296.2 and 2.6 min- Compound No. 69a, 402.2 and 4.3 min- Compound No. 77a, 361.2 and 4.4 min- Compound No. 70a, 368.5 and 4.8 min- Compound No. 2, or 389.3 and 5.0 min- Compound No. 75a, wherein the measuring is performed by LC/MS equipped with ACQUITY UPLC BEH C18 (1.7 μm, 2.1 mm×100 mm; manufactured by Waters) as the LC column and LCT Premier (manufactured by Waters) as the MS machine, and wherein the m/z value contains an error range of ±0.1 and the retention time contains an error range of ±0.1 min, and wherein the urine sample is processed to form 250 μL of supernatant of the urine sample, which has been centrifuged at 2500 rpm for 15 min at 4° C. by a centrifugal machine, is mixed with 750 μL of 0.1% (w/w) formic acid aqueous solution to which 0.09% (w/w) sodium azide has been added to obtain a mixed solution, and the mixed solution is measured under a condition of a column temperature is 40° C.;

an automatic sampler temperature is 4° C.;

an injection amount of measuring sample is 5 μL;

a flow rate is 0.30 mL/min;

analysis time is 17 min; and gradient conditions (A/B (v/v %)) of a mobile phase (A) 6.5 mM aqueous solution of ammonium hydrogencarbonate and a mobile phase (B) 6.5 mM aqueous solution of ammonium hydrogencarbonate in 95% (w/v) methanol are 0-4 min (100/0), 4-4.5 min (30/70), 4.5-10 min (2/98), and 10-17 min (100/0).

8. A method for diagnosing and treating irritable bowel syndrome in a subject, the method comprising:

(i) a step of diagnosing the subject with irritable bowel syndrome by obtaining a urine sample of the subject, measuring a concentration of a biomarker in the urine sample of the subject, and comparing the concentration with that of a healthy individual, wherein the subject is diagnosed with irritable bowel syndrome when the concentration of the biomarker in the urine sample of the subject is less than that of the healthy individual, and (ii) a step of administering a therapeutic agent for treating irritable bowel syndrome to the diagnosed subject, wherein the biomarker is selected from the group consisting of compounds whose m/z value and retention time, measured by LC/MS, are:

(1) 264.3 and 3.9 min- Compound No. 5, 205.2 and 2.6 min- Compound No. 10, 189.2 and 2.7 min- Compound No. 11, 152.0 and 1.6 min- Compound No. 24, 133.1 and 0.7 min- Compound No. 25, 181.1 and 1.0 min- Compound No. 28, or 197.0 and 1.7 min- Compound No. 29, wherein the measuring is performed by LC/MS equipped with ACQUITY UPLC BEH C18 (1.7 μm, 2.1 mm×150 mm; manufactured by Waters) as an LC column and 4000QTRAP (manufactured by AB SCIEX) as an MS machine, and wherein the m/z value contains an error range of ±0.1 and the retention time contains an error range of ±0.1 min, and wherein the urine sample is processed to form 250 μL of supernatant of the urine sample, which has been centrifuged at 2500 rpm for 15 min at 4° C. by a centrifugal machine, is mixed with 750 μL of 0.1% (w/w) formic acid aqueous solution to which 0.09% (w/w) sodium azide has been added to obtain a mixed solution, and the mixed solution is measured under a condition of a column temperature is 40° C.;

an automatic sampler temperature is 4° C.;

an injection amount of measuring sample is 5μL;

a flow rate is 0.30 mL/min;

analysis time is 21 min; and gradient conditions (A/B (v/v %)) of a mobile phase (A) 0.1% (w/w) formic acid aqueous solution and a mobile phase (B) acetonitrile are 0-7 min (100/0), 7-14 min (0/100), and 14-21 min (100/0), and (2) 419.9 and 0.6 min- Compound No. 59a, 537.2 and 2.9 min- Compound No. 61a, or 446.1 and 4.2 min- Compound No. 60a, wherein the measuring is performed by LC/MS equipped with ACQUITY UPLC BEH C18 (1.7 μm, 2.1 mm×100 mm; manufactured by Waters) as the LC column and LCT Premier (manufactured by Waters) as the MS machine, and wherein the m/z value contains an error range of ±0.1, and the retention time contains an error range of ±0.1 min, and wherein the urine sample is processed to form 250 μL of supernatant of the urine sample, which has been centrifuged at 2500 rpm for 15 min at 4° C. by a centrifugal machine, is mixed with 750 μL of 0.1% (w/w) formic acid aqueous solution to which 0.09%

(w/w) sodium azide has been added to obtain a mixed solution, and the mixed solution is measured under a condition of a column temperature is 40° C.;
an automatic sampler temperature is 4° C.;
an injection amount of measuring sample is 5 μL;
a flow rate is 0.30 mL/min;
analysis time is 17 min; and
gradient conditions (A/B (v/v %)) of a mobile phase (A) 0.1% (w/w) formic acid aqueous solution, and a mobile phase (B) 0.1% (w/w) formic acid methanol solution are 0-4 min (100/0), 4-4.5 min (30/70), 4.5-10 min (2/98), and 10-17 min (100/0), and (3) 342.1 and 1.2 min- Compound No. 81a, 260.2 and 1.8 min- Compound No. 80a, 340.1 and 2.1 min- Compound No. 76a, 296.2 and 2.6 min- Compound No. 69a, 402.2 and 4.3 min- Compound No. 77a, 361.2 and 4.4 min- Compound No. 70a, 368.5 and 4.8 min- Compound No. 2, or 389.3 and 5.0 min- Compound No. 75a, wherein the measuring is performed by LC/MS equipped with ACQUITY UPLC BEH C18 (1.7 μm, 2.1 mm×100 mm; manufactured by Waters) as the LC column and LCT Premier (manufactured by Waters) as the MS machine, and wherein the m/z value contains an error range of ±0.1 and the retention time contains an error range of ±0.1 min, and wherein the urine sample is processed to form 250 μL of supernatant of the urine sample, which has been centrifuged at 2500 rpm for 15 min at 4° C. by a centrifugal machine, is mixed with 750 μL of 0.1% (w/w) formic acid aqueous solution to which 0.09% (w/w) sodium azide has been added to obtain a mixed solution, and the mixed solution is measured under a condition of a column temperature is 40° C.;
an automatic sampler temperature is 4° C.;
an injection amount of measuring sample is 5 μL;
a flow rate is 0.30 mL/min;
analysis time is 17 min; and
gradient conditions (A/B (v/v %)) of a mobile phase (A) 6.5 mM aqueous solution of ammonium hydrogencarbonate and a mobile phase (B) 6.5 mM aqueous solution of ammonium hydrogencarbonate in 95% (w/v) methanol are 0-4 min (100/0), 4-4.5 min (30/70),4.5-10 min (2/98), and 10-17 min (100/0).

9. The method according to claim 7, wherein the biomarker is selected from the group consisting of dehydroepiandrosterone sulfate (Compound No. 2), 2,7,8-trimethyl-2-β-carboxyethyl)-6-hydroxychroman (Compound No. 5), xanthurenic acid (Compound No. 10), kynurenic acid (Compound No. 11), gentisic acid (Compound No. 24), glycylglycine (Compound No. 25), homovanillic acid (Compound No. 28), and vanillylmandelic acid (Compound No. 29).

10. The method according to claim 8, wherein the biomarker is selected from the group consisting of xanthurenic acid (Compound No. 10), gentisic acid (Compound No. 24), glycylglycine (Compound No. 25), homovanillic acid (Compound No. 28), and vanillylmandelic acid (Compound No. 29).

* * * * *

UNITED STATES PATENT AND TRADEMARK OFFICE
CERTIFICATE OF CORRECTION

PATENT NO. : 11,215,607 B2
APPLICATION NO. : 15/119930
DATED : January 4, 2022
INVENTOR(S) : Shin Fukudo et al.

It is certified that error appears in the above-identified patent and that said Letters Patent is hereby corrected as shown below:

In the Claims

In Claim 1, Column 26, Line 58, after "patient,", insert --¶--.

Signed and Sealed this
Twenty-fourth Day of May, 2022

Katherine Kelly Vidal
Director of the United States Patent and Trademark Office